United States Patent
Ichimura et al.

(10) Patent No.: US 8,546,068 B2
(45) Date of Patent: Oct. 1, 2013

(54) METHOD FOR FABRICATING MICROBEADS AND MICROBEADS

(75) Inventors: Mari Ichimura, Kanagawa (JP); Kenzo Machida, Tokyo (JP); Noriyuki Kishii, Kanagawa (JP); Masanobu Tanaka, Kanagawa (JP)

(73) Assignee: Sony Corporation, Tokyo (JP)

( * ) Notice: Subject to any disclaimer, the term of this patent is extended or adjusted under 35 U.S.C. 154(b) by 54 days.

(21) Appl. No.: 13/120,967

(22) PCT Filed: Sep. 4, 2009

(86) PCT No.: PCT/JP2009/065508
§ 371 (c)(1),
(2), (4) Date: Mar. 25, 2011

(87) PCT Pub. No.: WO2010/038579
PCT Pub. Date: Apr. 8, 2010

(65) Prior Publication Data
US 2011/0183272 A1 Jul. 28, 2011

(30) Foreign Application Priority Data
Sep. 30, 2008 (JP) .................................. 2008-252329

(51) Int. Cl.
*G03F 7/26* (2006.01)
(52) U.S. Cl.
USPC ........................... 430/324; 430/329; 430/256
(58) Field of Classification Search
USPC .......................................... 430/324, 329, 256
See application file for complete search history.

(56) References Cited

U.S. PATENT DOCUMENTS

| 6,268,222 | B1 | 7/2001 | Chandler et al. | |
|---|---|---|---|---|
| 2003/0153092 | A1* | 8/2003 | Skinner et al. | 436/174 |

FOREIGN PATENT DOCUMENTS

| JP | 1992-173841 | 6/1992 |
|---|---|---|
| JP | 2004-501344 | 1/2001 |
| JP | 3468750 | 9/2003 |
| JP | 2004-20280 | 1/2004 |
| JP | 2008-536699 | 9/2008 |
| WO | 01/78889 | 10/2001 |
| WO | 2006/113492 | 10/2006 |
| WO | 2006/113492 A2 | 10/2006 |

OTHER PUBLICATIONS

Pregibon et al., "Multifunctional Encoded Particles for High-Throughput Biomolecule Analysis", Science, Mar. 9, 2007, pp. 1393-1396, vol. 315.
International Search Report mailed Nov. 24, 2009, corresponding to PCT/JP2009/065508.
Extended European Search Report issued in connection with European Application No. 09817616.7, dated Apr. 4, 2013. (6 pages).

* cited by examiner

*Primary Examiner* — Kathleen Duda
*Assistant Examiner* — Caleen Sullivan
(74) *Attorney, Agent, or Firm* — K&L Gates LLP

(57) ABSTRACT

In one example embodiment, a method fabricates microbeads, which can supply a bead set containing a various types of microbeads and having distinct populations of the respective types of microbeads. In one example embodiment, the method includes forming a hydrophilic layer made of a hydrophilic organic material on a substrate. In one example embodiment, the method includes laminating on the hydrophilic layer a thin film capable of being peeled off in the form of microbeads. In one example embodiment, the method includes forming the thin film in a given configuration by photolithography. In one example embodiment, the method includes solid-phasing a given substance on the post-formed thin films. In one example embodiment, the method includes peeling off the post-formed thin films, which have been solid-phased with the substance, from the substrate along with at least a part of the hydrophilic layer to obtain microbeads.

17 Claims, 5 Drawing Sheets

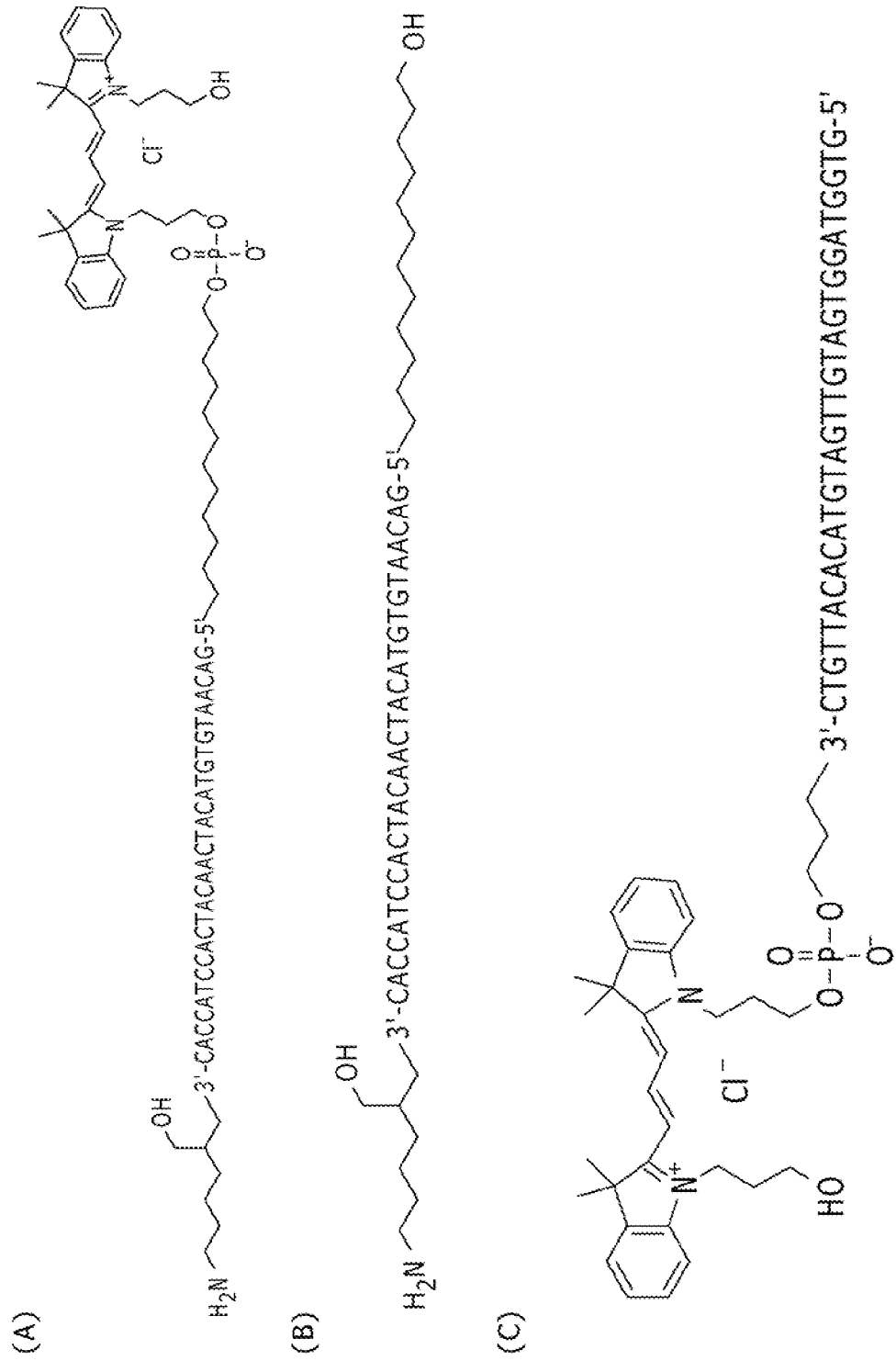

METHOD FOR FABRICATING MICROBEADS AND MICROBEADS

CROSS REFERENCE TO RELATED APPLICATIONS

The present application is a National Stage of International Application No. PCT/JP2009/065508 filed on Sep. 4, 2009, which claims priority to Japanese Patent Application No. 2008-252329 filed on Sep. 30, 2008, the entire contents of which are being incorporated herein by reference

BACKGROUND

In biochemical assays for nucleic acids, proteins and the like, particulate carriers called "microbeads" have been used. For example, in assays of nucleic acids, there are used microbeads wherein a probe nucleic acid chain having a complementary base sequence relative to a target nucleic acid chain is solid-phased on a surface thereof. The target nucleic acid chain is isolated based on the interaction between the target nucleic acid chain and the probe nucleic acid chain. In protein assays, microbeads, on which an antibody relative to a target protein is solid-phased on a surface thereof, are used to isolate the target protein in a similar way.

In the biochemical assays making use of these microbeads, a higher throughput has been recently demanded, for which there are being developed techniques of realizing high-speed assays.

In Patent Document 1, for example, there is disclosed "A method for detecting analytes among a number of analytes in a sample, the first-mentioned analytes being recognized with the respective analytical reactants, the method including: (a) bringing, into contact with a sample, a number of populations of fluorescent particles, which populations, respectively, have different fluorescent signals and different analytical reactants wherein the analytical reactant specifically binds to one analyte in the sample and each fluorescent particle has, on a surface thereof, at least one nanoparticle labeled with each corresponding fluorescent dye, (b) adding a labeling reagent to the sample, (c) detecting the label to analyse the fluorescent particle indicating the binding of the analytical reactant with the analyte, and (d) simultaneously determining the populations of the fluorescent particles bound to the respective analytes from the function of the different fluorescent signals associated with the respective populations".

In "Suspension Array Technology" provided by Luminex Trading, Inc., based on this technique, two types of fluorescent dyes are labeled on a microbead while imparting a change in emission color, thereby enabling 100 types of microbeads in maximum to be discriminated from one another. According to the "Suspension Array Technology," when different probe nucleic acid chains and antibodies are, respectively, solid-phased on 100 types of microbeads, it becomes possible to simultaneously isolate and detect 100 different types of nucleic acid chains and proteins through one assay.

In the above document, it is recited that "the populations of the fluorescent particles are further determined depending on the sizes and shapes thereof" and it is disclosed that for the additional parameters of discriminating microbeads, the size and shape of the bead can be adopted (see Paragraphs 0037 and the like of the document). Further to this, in Non-Patent Document 1, there is described a method of making a number of differently shaped microbeads according to photolithography in a flow path. According to this method, fabrication of greater than one million types of microbeads becomes possible.

Patent Document 1: Japanese Patent Publication No. 3468750

Non-Patent Document

Non-Patent Document 1: Multifunctional encoded particles for high-throughput biomolecule analysis. Science, 2007, Mar. 9; 315(5817): 1393-6.

SUMMARY

This disclosure relates to a method for fabricating microbeads and also to microbeads. More particularly, the disclosure relates to a method for fabricating microbeads wherein microbeads solid-phased on a surface thereof with a given type of substance are made according to photolithography on substrate, and the like.

The super-diversity of microbeads disclosed in the Patent Document 1 and the Non-patent Document 1 and having different fluorescent characteristics and shapes are, respectively, solid-phased with probe nucleic acid chains or antibodies differing from one another, and mixed for use as a bead set. This bead set and a sample containing target nucleic acid chains are mixed and rinsed, followed by detection of the respective microbeads and the target nucleic acid chains captured on the surface thereof by optical or magnetic or electric signals.

In order to obtain a high analytical accuracy, it is necessary that the number of the microbeads present in the bead set be clear. For instance, for the simplest example where signal intensities of two types of microbeads are compared with each other, if the numbers of both types of microbeads (populations) contained in a bead set are not distinct, the resulting signal intensities cannot be compared with each other. In this case, for the accurate comparative analysis of the signal intensities, it is desirable that both types of microbeads be present at equal numbers, or unless the numbers are equal, a ratio in number between both types of beads needs to be known.

The populations in a bead set have been hitherto adjusted by quantitatively determining the respective microbeads after preparation on the basis of the weight and absorbance and mixing them. With this method, however, it is not possible to exactly adjust the numbers of the respective types of beads and thus the populations are caused to be varied, resulting in an impediment to obtaining a high analytic accuracy.

Therefore, the disclosure has for its primary object the provision of a method for fabricating microbeads capable of supplying a bead set containing a wide variety of microbeads wherein populations of the respective types of microbeads are distinct.

In order to solve the above problem, the disclosure provides a method for fabricating microbeads, which including the steps of forming a hydrophilic layer made of a hydrophilic organic material on a substrate, laminating, on the hydrophilic layer, a thin film capable of being peeled off as microbeads, forming the thin film into a given shape by photolithography, subjecting a given type of substance to solid-phasing on post-formed thin films, peeling off the post-formed thin films, solid-phased with the substance, from the substrate along with at least a part of the hydrophilic layer to obtain microbeads. According to this fabrication method of microbeads, microbeads with arbitrary multiform morphologies can be fabricated in arbitrary numbers, respectively, by designing the shapes of photomask used in the photolithography.

In this microbead fabrication method, a hydrophilic organic material dissolved in a solvent is coated onto a substrate and dried to form the hydrophilic layer. Thereafter, in the peeling-off step, a solvent that is set at a temperature at which the hydrophilic organic material can be re-dissolved is used to dissolve part of the hydrophilic layer, or the post-formed thin film is peeled off along with at least a part of the hydrophilic layer by ultrasonic treatment, thereby obtaining microbeads. In this way, there can be obtained microbeads, which have a steric configuration provided with substantially parallel opposing faces and wherein a given type of substance is solid-phased only on one of the faces and the other face is imparted at least partially with hydrophilicity.

In this case, the hydrophilic layer is formed of one or more of hydrophilic organic materials selected from polyvinyl alcohol, starch, dextrin, amylose, gelatin, agar, carrageenan, pectin, locust bean gum, and photosensitive hydrophilic resins.

The microbead fabrication method may further include the step of forming a sacrificial layer on the substrate. In the case, the hydrophilic layer is laminated on the sacrificial layer. In the peeling step, the sacrificial layer is physically or chemically eroded to peel off the post-formed thin film along with the hydrophilic layer to obtain microbeads. In this way, there can be obtained, like the above case, microbeads, which have a steric configuration provided with two substantially parallel opposing faces and wherein a given type of substance is solid-phased only on one of the faces and hydrophilicity is imparted on at least a part of the other face.

In this case, the hydrophilic layer is formed of one or more of hydrophilic organic materials selected from photosensitive hydrophilic resins, polyvinyl alcohol, starch, dextrin, amylose, gelatin, agar, carrageenan, pectin and locust bean gum.

The sacrificial layer can be formed of a fluorine-based organic material or a polyimide organic material, or may be formed of the same type of hydrophilic organic material or a different type of hydrophilic organic material as used for the hydrophilic layer.

Where the sacrificial layer is formed by use of a fluorine-based organic material, this sacrificial layer made of the fluorine-based organic material is sublimated or dissolved by use of a fluorine-based solvent in the peeling-off step thereby permitting the post-formed thin film to be peeled off from the substrate along with the hydrophilic layer to obtain microbeads.

Where the sacrificial layer is formed by use of a polyimide organic material, the sacrificial layer made of the polyimide organic material is dissolved in an aprotic solvent in the peeling-off step, thereby permitting the post-formed thin film to be peeled off from the substrate along with the hydrophilic layer to obtain microbeads.

Where the sacrificial layer is formed by use of the same type of hydrophilic organic material or different type of hydrophilic organic material as used for the hydrophilic layer, the sacrificial layer made of the hydrophilic organic material is dissolved in a solvent set at a temperature, at which the hydrophilic organic material is able to be re-dissolved, in the peeling-off step, or ultrasonic treatment is carried out thereby permitting the post-formed thin film to be peeled off from the substrate along with the hydrophilic layer to obtain microbeads.

In this microbead fabrication method, the solid-phasing step should preferably be carried out by chemical synthesis of the substance on the thin film. More particularly, for the substance, one or more of biopolymers selected from given sequences of nucleic acids or peptides and sugar chains are solid-phased. Preferably, regions among the post-formed thin films are subjected to water repellent finish after the forming step but prior to the solid-phasing step. The water repellent finish is able to prevent solutions dropped over the surface of the post-formed thin film from mixing with one another, thereby enabling desired types of substances to be solid-phased on the respective microbeads.

In the microbead fabrication method, the thin film is favorably formed by use of a photoresist or silicon dioxide.

In the practice of the disclosure, the "substance" to be solid-phased on the thin film, i.e. on the microbead, widely includes those substances capable of being interacted with a target nucleic acid or target protein, which is a target under analysis in the biochemical assay using microbeads. This substance is preferably a biopolymer selected from given sequences of nucleic acids or peptides and sugar chains and should include molecules capable of being interacted with target nucleic acids or the like. Where the "biopolymer" is directed to a nucleic acid, the nucleic acid should be one having a given base sequence. The "interaction" means duplex formation between nucleic acids having complementary base sequences. Where the "biopolymer" is directed to a peptide, the peptide should be one with a given amino acid sequence. The "interaction" in this case is, for example, a protein-protein bonding such as a bonding between an acceptor protein and a ligand protein or a bonding between an antigen and an antibody. Moreover, if the biopolymer is directed to a sugar chain, the sugar chain should be a saccharide-binding chain or this binding chain further bound with a lipid or protein and is an oligosaccharide, a sugar lipid or a sugar protein. Besides, this "substance" covers a variety of compounds in the form of a small molecule. These compounds are capable of being bound with a target nucleic acid or a target protein, which is a target under biochemical analysis and are ones, which are capable of promoting or impeding the function of a nucleic acid or protein and become so-called "seed compound" in the field of drug discovery. It will be noted that the "nucleic acid" used herein includes, aside from DNA and RNA, nucleic acid analogues (e.g. LNA (Locked Nucleic Acid)) obtained by modifying the structures of ribose moieties thereof.

According to the disclosure, there is provided a method for fabricating microbeads, which is able to provide a bead set including a variety of microbeads wherein populations of the respective microbeads are distinct.

BRIEF DESCRIPTION OF DRAWINGS

FIG. 9 is a view showing structures of oligo DNA's and target oligo DNA's solid-phased on microbead surfaces in Examples 1 and 3 wherein (A) is for oligo DNA-1, (B) is for oligo DNA-2 and (C) is for oligo DNA-3.

DETAILED DESCRIPTION

Preferred example embodiments for carrying out the disclosure are described with reference to the drawings. It will be noted that the example embodiments illustrated below are an instance of typical example embodiments of the disclosure whose scope should not be construed as narrowly limited thereto.

Microbeads (1) Configuration and Population

Figure 1:
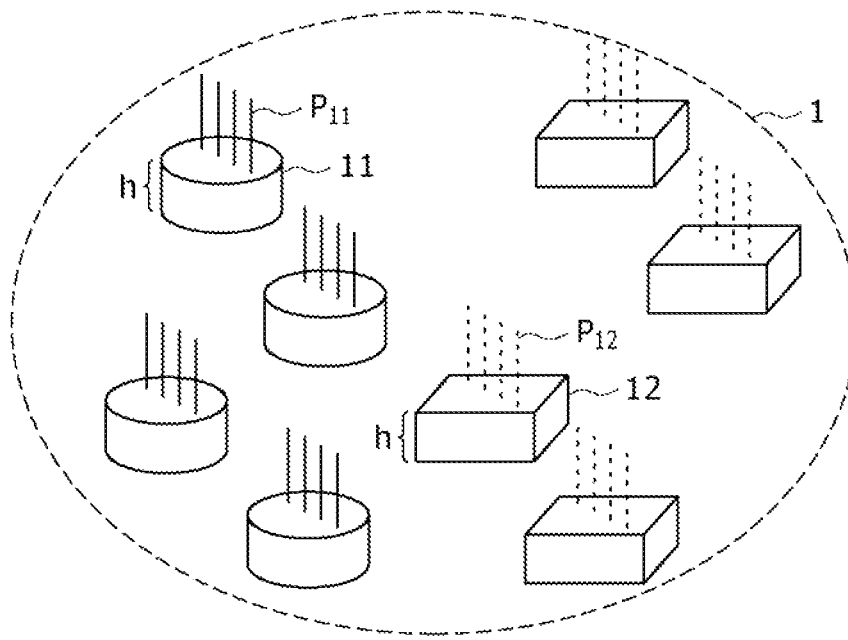
FIG. 1 is a schematic view showing microbeads and a bead set obtained according to a microbead fabrication method of the disclosure.

FIG. 1 is a schematic view showing microbeads and a bead set obtained by a microbead fabrication method according to the disclosure.

In FIG. 1, a bead set indicated by reference numeral 1 is made up of two types of microbeads including substantially cylindrical microbeads 11 and substantially cubic microbeads 12. The microbeads obtained according to the microbead fabrication method of the disclosure have such a steric configuration provided with two substantially parallel opposing faces.

The microbeads 11 and the microbeads 12 differ in whole shape and can be discriminated from each other by an ordinary image distinction means based on the difference in the configuration. The bead set 1 includes given numbers of the microbeads 11 and the microbeads 12 (four in each group in FIG. 1).

The microbead set obtained according to the microbead fabrication method of the disclosure is characterized by including plural types of microbeads differing in configuration in given numbers and the numbers are precise.

The numbers (populations) of the respective types of microbeads present in the bead set 1 can be arbitrarily set. For simplicity, FIG. 1 shows two types of microbeads, substantially cylindrical and substantially cubic, each including four beads. Three or more types of microbeads may be contained in the bead set 1 and the numbers of the respective types of microbeads may differ from one another. The configurations of the respective types of microbeads may be arbitrarily designed in so far as they are discriminable by ordinary image distinction means. The "configuration" used herein includes, aside from the whole configuration of bead, fine shapes processed in or on the bead surface (typically, so-called "bar code").

Probe

On the surface of the microbeads 11, there is solid-phased a biopolymer such as a nucleic acid or peptide, or a sugar chain, or a small molecule (hereinafter referred to as "nucleic acid or the like") indicated by symbol $P_{11}$ in FIG. 11. It is characterized that these substances are solid-phased only on one of the two substantially parallel opposing faces (an upper face in the figure) among the faces of the microbeads 11.

The nucleic acid or the like $P_{11}$ may be provided as a given base sequence or amino acid sequence depending on the type of analytical subject. Moreover, the nucleic acid or the like $P_{11}$ may be provided as a sugar chain or a variety of compounds. Hereinafter, the case where a nucleic acid or peptide is used as the nucleic acid or the like $P_{11}$ is primarily described.

For instance, in case where a nucleic acid is an analytical subject, a nucleic acid chain having a complementary base sequence relative to its target nucleic acid chain is solid-phased as the nucleic acid or the like $P_{11}$. This enables the target nucleic acid chain in a sample to be captured and isolated on the microbeads 11 through hybridized (duplex) formation with the nucleic acid or the like $P_{11}$. It will be noted that the number (length) of the bases of the nucleic acid chain or the like $P_{11}$ is arbitrary, and the number of the bases is not critical in so far as the base sequence of the target nucleic acid chain has a complementary base sequence in at least a part thereof and duplex formation is possible. In general, the number of bases in the nucleic acid chain or the like $P_{11}$ is several to several tens, preferably about 10 to 30.

For instance, in case where a protein is an analytical subject, a peptide (e.g. a partial amino acid sequence of a ligand protein) capable of interaction with the target protein (e.g. a receptor protein) is solid-phased as the nucleic acid or the like $P_{11}$. This enables the target protein in a sample to be captured and isolated on the microbeads 11 through the interaction with the nucleic acid or the like $P_{11}$.

On the other hand, a nucleic acid or the like indicated by symbol $P_{12}$ in FIG. 1 is solid-phased on the surface of the microbead 12. The nucleic acid or the like $P_{12}$ may be provided as a given base sequence or amino acid sequence depending on the type of nucleic acid or protein that is an analytical subject and also as a sugar chain or a variety of compounds as well. In the microbeads 12, these substances are solid-phased on one (an upper face) of two faces that are substantially parallel and opposing with each other.

When, for example, different types of substances such as nucleic acids or peptides having different base sequences or amino acid sequences are provided as the nucleic acid or the like $P_{11}$ to be solid-phased on the surface of the microbeads 11 and the nucleic acid or the like $P_{12}$ to be solid-phased on the surface of the microbeads 12, different types of target nucleic acids or target proteins can be captured and isolated on the respective types of microbeads.

The target nucleic acids or target proteins captured and isolated with the microbeads 11, 12 are detected with fluorescent dye labels such as through optical detection and simultaneously, the microbeads 11, 12 are discriminated by image distinction means, thereby enabling two types of target nucleic acids or target proteins to be analyzed at the same time.

For example, with the case of a single nucleotide polymorphism (SNP) analysis, a base sequence of the nucleic acid or the like $P_{11}$ is determined as a base sequence corresponding to one SNP and a base sequence of the nucleic acid or the like $P_{12}$ is as a base sequence corresponding to another SNP. This bead set is mixed with a sample and the signals on the microbeads 11 (e.g. fluorescent signal intensity) and the signals on the microbeads 12 are compared with each other, thereby making it possible to determine a ratio between the SNP types of nucleic acids contained in the sample.

Hydrophilicity

Of the two substantially parallel opposing faces of the microbeads 11, 12, the face (a bottom face in the figure) where neither nucleic acid or the like $P_{11}$ nor $P_{12}$ is solid-phased is imparted with hydrophilicity ascribed to "hydrophilic layer" described hereinafter.

The microbeads are usually formed of a hydrophobic material so as to keep its configuration in an aqueous solution on use. The microbeads 11, 12 of the disclosure are also formed of a hydrophobic thin film material by use of photolithography described hereinafter.

However, where microbeads are formed of a hydrophobic material, the bead surface becomes hydrophobic, thereby presenting a problem of mutual coagulation of microbeads ascribed to hydrophobic interaction. The mutual coagulation of the microbeads disenables the nucleic acids or the like $P_{11}$, $P_{12}$ to be solid-phased. Additionally, when they are subjected to analysis, the discrimination of their configurations with an image distinction means becomes impossible and efficient capture and isolation of target nucleic acids or target proteins cannot be realized, so that the accurate results of the analysis cannot be obtained.

This is why the microbeads 11, 12 are so configured as to impart hydrophilicity at one (a bottom face in the figure) of the two substantially parallel opposing faces thereof and thus prevent the mutual coagulation of the microbeads.

Bead Set

In this way, the bead set 1 is constituted of plural types of microbeads having different configurations wherein nucleic acid chains or peptides whose base sequences or amino acid sequences differ from one another are solid-phased. This makes it possible to simultaneously analyze a plurality of target nucleic acids or proteins present in a sample.

As having set out hereinbefore, in order to obtain a high analysis accuracy, it is necessary that the numbers of the respective types of microbeads contained in a bead set be distinct. For instance, in the instance of the afore-described SNP analysis, if the populations of the microbeads 11, 12 in the bead set 1 are not known, it is not possible to exactly determine a ratio between the SNP types of nucleic acids in the sample by comparison of the signals obtained therefrom.

In this regard, with the bead set 1 where the numbers of the plural types of microbeads having different configurations are distinct, the numbers of the microbeads 11 and the microbeads 12 can be exhaustively coincided with each other, thereby setting at the same number. Thus, the signals obtained from both are compared with each other, thereby enabling a high analysis accuracy to be obtained.

Microbead Fabrication Method I

Case of a Hydrophilic Layer Provided as a Sacrificial Layer

Figure 2:
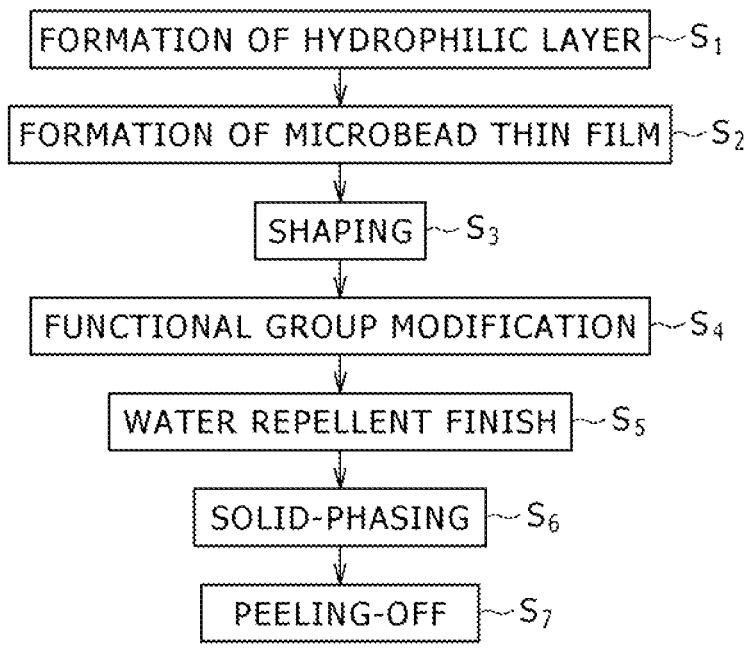
FIG. 2 is a flow chart showing the steps of the microbead fabrication method according to one example embodiment of the disclosure.

Referring to FIG. 2, a first example embodiment related to a fabrication method of microbeads and a bead set is now described. FIG. 2 is a flow chart showing the steps of a microbead fabrication method according to the first example embodiment.

Film-Forming Step of a Hydrophilic Layer

In FIG. 2, "hydrophilic layer-forming step" indicated by symbol $S_1$ is a step wherein "hydrophilic layer" is formed on a substrate so as to impart hydrophilicity to a bottom face of a microbead. In the microbead fabrication method according to this example embodiment, the hydrophilic layer function as a so-called sacrificial layer for peeling microbeads therefrom.

The substrate used includes, for example, a glass substrate, a silicon substrate or the like. The material of the substrate is not critical and those materials ordinarily used in photolithographic techniques are appropriately adopted.

The "sacrificial layer" used in the disclosure means a layer of a material capable of undergoing physical or chemical erosion in a peeling step $S_7$ described hereinafter. A thin film capable of being peeled off as microbeads is formed on this sacrificial layer as an upper layer and subjected to erosion of the sacrificial layer in the peeling step to obtain microbeads.

The sacrificial layer should preferably be one that does not undergo erosion and damage to such an extent that the microbeads on a substrate are peeled off by means of chemicals employed in bead fabrication steps prior to the peeling step, especially in a step of solid-phasing a nucleic acid or the like.

The sacrificial layer should preferably be one that is capable of undergoing erosion in the peeling step without denaturing or releasing the nucleic acid or the like solid-phased on the microbeads. If the nucleic acid or the like solid-phased on the microbeads undergoes denaturation, damage, release and the like, a target nucleic acid or target protein cannot be captured on the beads. Accordingly, the sacrificial layer used should be one that is able to undergo erosion while keeping the interactivity with target nucleic acids or target proteins such as nucleic acids or the like solid-phased on the microbeads.

In the microbead fabrication method according to the first example embodiment, the hydrophilic layer imparting hydrophilicity to the bottom face of the microbeads is functioned also as a so-called sacrificial layer. This hydrophilic layer is formed by use of a hydrophilic organic material. More particularly, a hydrophilic organic material dissolved in a solvent is coated onto a substrate and dried to form a hydrophilic layer. The hydrophilic organic material may be coated by spin coating, dip coating, screen printing, a spraying method, ink jet printing or the like.

The thus formed hydrophilic layer may be partially dissolved by use of a solvent set at a temperature, at which the hydrophilic organic material is able to be re-dissolved in the peeling-off step $S_7$ to be described later. Accordingly, the hydrophilic organic material used should preferably be one that is not re-dissolved, for example, in the vicinity of room temperature (30° C.) but is re-dissolved in the vicinity of 45° C. or over. More particularly, there can be used, as a hydrophilic organic material re-dissolved in hot or warm water, one or more of materials selected from water-soluble polymers such as polyvinyl alcohol, starch, dextrin, amylose and the like. Especially, polyvinyl alcohol is preferred for use as a sacrificial layer because after being coated onto a substrate after dissolution in a heated solvent and dried, it is not re-dissolved unless re-heated.

Besides, there may be adopted, as the hydrophilic organic material, gelatin (whose main component is collagen), agar (whose main components include agarose and agaropectin), carageenan (whose main components include galactose and anhydrogalactose), pectin (whose main components include galacturonic acid and galacturonic acid methyl ester), locust bean gum (whose main component is galactomannan), photosensitive hydrophilic resins and the like.

Film-Forming Step of Forming a Microbead Thin Film

In FIG. 2, "microbead thin film-forming step" indicated by symbol $S_2$ is a film-forming step of forming a thin film made of a material for microbead laminated on the hydrophilic layer formed on the substrate.

The thin film made of a variety of polymers, silicon dioxide or a metal (such as aluminum, chromium, gold, silver or the like) used as a microbead material is formed. The film formation may be carried out by hitherto known techniques such as coating techniques using spin coaters or slit coaters or blowing, or vapor depositions such as a physical vapor deposition (PVD) and a chemical vapor deposition (CVD) although depending on the type of material for the thin film. The thickness of the thin film is appropriately set depending on the thickness of fabricated microbeads (see symbol h in FIG. 1).

As the material for thin film, there are favorably used photoresists including epoxy resists such as SU-8, polyimide resists, acrylic resists, novolac resists and the like. Using a polymeric photoresist thin film, microbeads can be fabricated more inexpensively than with the case of a silicon dioxide thin film or a metal thin film, and microbeads with a low specific gravity are obtained. When analyzed, microbeads are mixed with a sample and is dispersed in a liquid phase. At this stage, when the specific gravity of the microbeads is great, it is not possible to keep the dispersed state in the liquid phase over a prolonged period.

SU-8 is preferred among the polymers. SU-8 is a chemically amplified epoxy-based, negative photoresist. SU-8 was developed by IBM of U.S.A., for use as a material for forming a microstructure in combination of a resist ultrathin film formation technique and a photolithographic technique.

When using SU-8, the thickness can be readily controlled by forming a film by spin coating. SU-8 exhibits high optical transparency and is provided with good solubility resistance and high temperature resistance to a variety of solvents, acids and alkalis. Accordingly, the use of SU-8 enables microbeads having different thicknesses to be fabricated in a simple way and ensures stable performance in the fabrication procedure of microbeads and also in the analytical procedure using the microbeads.

Forming Step

"Forming step" indicated by symbol $S_3$ in FIG. 2 is a step wherein the thin film formed in the film-forming step $S_2$ is formed into a desired shape by photolithography. This step is carried out by different procedures for (3-1) a film of a resist such as of SU-8 and for (3-2) a film of silicon dioxide or a variety of metals as a material for microbead. Where a resist such as SU-8 is used as a microbead material and subjected to film formation A thin film formed in the film-forming step $S_2$ is initially heated, if necessary, and solidified (pre-baked). Next, a photomask (hereinafter referred to simply as "mask") having microbead configurations drawn therein is used and subjected to light exposure. The exposed substrate is immersed in a liquid developer to remove unnecessary regions of the thin film, followed by rinsing with a liquid rinse agent (isopropyl alcohol: IPA) to completely remove the unnecessary regions. Thereafter, post-baking is effected whereupon the configurations of microbeads appear in the thin film left on the substrate.

When the configuration in the mask is designed depending on the configuration of microbeads to be fabricated, microbeads having an arbitrary configuration can be formed on the substrate. Likewise, the arbitrary designing of the mask enables microbeads having different configurations to be formed in arbitrary numbers, respectively. Using a maskless exposure device, arbitrary numbers of microbeads having arbitrary configurations can be likewise formed without fabricating a photomask.

Where Film Formation is Performed Using Silicon Dioxide or a Variety of Metals as a Microbead Material An ordinarily employed resist is initially spin coated onto a surface of the thin film and, if necessary, pre-baked. Next, light exposure is carried out using such a mask as in above. The exposed substrate is immersed in a liquid developer to remove unnecessary regions of the resist, followed by rinsing with a liquid rinse agent (mainly, ultrapure water) several times to remove the unnecessary regions and post-baking. Thereafter, the thin film is subjected to patterning by etching and the resist is completely removed. This enables configurations of microbeads to appear in the thin film left on the substrate.

Functional Group Modification Step

"Functional group modification step" indicated by symbol $S_4$ in FIG. 2 is a step of modifying, with a functional group, the surface of the thin film formed in the forming step $S_3$.

The thin film formed on the substrate in the film-forming step $S_2$ is left only at portions thereof serving as microbeads by the forming step $S_3$, and the other portions are removed. In the functional group modification step $S_4$, functional group modification for a solid-phasing step illustrated in the next place is carried out on the surface of the thin film at the portions serving as microbeads.

The modifying functional group may be, for example, a hydroxyl group, an amino group, a carboxyl group, an isothiocyanate group, an epoxy group, a maleinimide group or the like. In the conventional manufacture of DNA chips or protein chips, the modification of the functional group on the substrate surface has been carried out in order to introduce a linker for solid-phasing a nucleic acid chain or a peptide on the substrate surface. In the practice of the disclosure, a similar technique may be adopted.

A specific example where the thin film surface is modified with a hydroxyl group is described. In this case, the substrate surface is initially treated with aminopropyltriethoxysilane and is subsequently immersed in dimethylformamide (DMF) dissolving γ-valerolactone and reacted, resulting in hydroxyl group modification. Alternatively, the substrate surface may be treated with glycidoxypropyltrimethoxysilane and immersed for reaction in a mixed solution of tetraethylene glycol admixed with a small amount of concentrated sulfuric acid, resulting in the modification.

This functional group modification step $S_4$ and a water repellent finishing step $S_5$ illustrated in the next place may be carried out in such a way that after the water repellent finishing step $S_5$ has been performed, the functional group modification step $S_4$ is then carried out. It will be noted that both of these steps are not always an essential step.

Water Repellent Finishing Step

"Water repellent finishing step" indicated by $S_5$ in FIG. 2 is a step of subjecting substrate regions among the thin films formed in the forming step $S_3$ to water repellent finish.

The thin film formed on the substrate in the film-forming step $S_2$ is so processed in the forming step $S_3$ that only portions serving as microbeads are left and the other portions are removed. In the water repellent finishing step $S_5$, water repellency necessary for a solid-phasing step subsequently illustrated is imparted to the substrate regions (substrate regions among the formed thin films) from which the thin film has been removed.

Impartment of the water repellency to the substrate regions from which the thin film has been removed contributes to preventing solutions dropped over the thin film portions serving as microbeads from mixing with one another.

The water repellent finish can be carried out, for example, in the following way. Initially, the thin film portions, which become microbeads, are once covered with an ordinarily employed resist, and the substrate regions from which the thin film has been removed is treated with triethoxy-1H,1H,2H,2H-tridecafluoro-n-octylsilane. Thereafter, the resist is removed and thus, water repellency is imparted to the substrate regions other than the microbead regions. Alternatively, after coverage with the resist, a fluorine resin may be spin coated and baked to impart water repellency.

It will be noted that where the functional group modification step $S_4$ is carried out after completion of the water repellent finishing step $S_5$, the functional group is modified only at the portions serving as microbeads after the water repellent finish of the substrate regions from which the thin film has been removed.

Solid-Phasing Step

"Solid-phasing step" indicated by symbol $S_6$ in FIG. 2 is a step of solid-phasing a nucleic acid or peptide on the surface of the thin films formed in the forming step $S_3$. It is to be noted that a substance to be solid-phased includes, aside from a nucleic acid or peptide, a sugar chain and a variety of compounds as set out hereinbefore.

At this stage, the thin films alone serving as microbeads are left on the substrate and the other substrate regions are imparted with water repellency. In the solid-phasing step $S_6$, a nucleoside solution or amino acid solution (hereinafter referred to generically as "monomer solution") is dropped on the thin film surface at the portions serving as microbeads and the nucleic acid or peptide is solid-phased by step synthesis on the thin film.

The step synthesis of a nucleic acid or peptide can be carried out by repeating a synthetic cycle of binding reaction wherein according to a desired base sequence or amino acid sequence, a monomer solution containing a corresponding base or amino acid is successively dropped on the thin film serving as a microbead.

For instance, where a nucleic acid is solid-phased, a monomer solution containing a nucleoside is dropped by means of a pipette, followed by reaction by dropping a 5-ethylthiotetrazole. After rinsing and drying, an oxidation solution is further dropped and reacted to convert the nucleoside phosphorous acid triester into a nucleoside phosphoric acid triester. After rinsing, an acetic acid anhydride/tetrahydrofuran mixed solution is dropped and reacted to cap the unreacted hydroxyl group introduced at the functional group modification step $S_4$. Moreover, after rinsing and drying, a dichloromethane solution containing dichloroacetic acid is dropped to eliminate the dimethoxytrityl protecting group from the 5'-hydroxyl group of the nucleoside bound to the substrate. Thereafter, rinsing and drying are carried out, followed by repeating the above steps of (a) nucleoside linkage, (b) rinsing, (c) oxidation, (d) rinsing, (e) removal of the dimethoxytrityl protecting group and (f) rinsing, and de-protection of the base moiety of the nucleic acid is finally performed. In this way, a nucleic acid having a desired base sequence can be solid-phased.

Where a peptide is solid-phased, for example, a monomer solution containing an amino acid whose α-amino group and side chain functional group have been appropriately protected is dropped and a condensation step carried out on the thin film according to various condensation methods is repeated, followed by final removal of various protecting groups. This enables a peptide having a desired amino acid sequence can be solid-phased.

The nucleic acid or peptide may be solid-phased by dropping a solution containing a preliminarily synthesized nucleic acid or peptide on a thin film at a portion serving as a microbead and binding with a functional group introduced at the functional group modification step $S_4$.

The monomer solution and the solution of a preliminarily synthesized nucleic acid or peptide can be dropped by spotting with a pipette or a microdispenser or inkjet spotting.

Peeling-Off Step

"Peeling-off step" indicated by symbol $S_7$ in FIG. 2 is a step of peeling off the post-formed thin film, on which a nucleic acid or peptide has been solid-phased, from the substrate.

In the microbead fabrication method according to the first example embodiment, the hydrophilic layer is imparted with a function of imparting hydrophilicity to the bottom face of a microbead and also with a function as a sacrificial layer. In this peeling-off step $S_7$, part of the hydrophilic layer is dissolved in and eroded with a solvent set at a temperature, at which the hydrophilic organic material is able to be re-dissolved. For instance, when a water-soluble polymer such as polyvinyl alcohol, starch, dextrin, amylose or the like is used as the hydrophilic organic material, it is re-dissolved with a solvent whose temperature is set in the vicinity of 45° C. or over.

The hydrophilic layer is eroded by the re-dissolution, whereupon the thin films laminated on the hydrophilic layer are peeled off as microbeads. At this time, part of the hydrophilic layer is left as not dissolved on the thin film surface at the side contacting the hydrophilic layer and thus, the surface of the microbead is imparted with hydrophilicity by means of this left hydrophilic layer.

When a hydrophilic organic material is dissolved in a heated solvent, part of the hydrophilic layer is, in most cases, left on the thin film surface. In order to impart satisfactory hydrophilicity to the bead surface, the re-dissolution of the hydrophilic layer should preferably be conducted under such conditions as to positively leave part of the hydrophilic layer on the thin film surface.

In the peeling-off step $S_7$ of this example embodiment, as a liquid remover for eroding the hydrophilic layer used as a so-called sacrificial layer, there can be used a solvent heated to a temperature capable of re-dissolving a hydrophilic organic material, preferably heated pure water. As stated hereinbefore, the sacrificial layer should preferably be one that can be eroded in the peeling-off step without denaturing or releasing the nucleic acid or the like solid-phased on the microbeads. In this example embodiment, pure water is used as a liquid remover, which enables microbeads to be obtained by erosion of the sacrificial layer while keeping interactivity of the nucleic acid or the like solid-phased on the microbead with a target nucleic acid, a target protein or the like. It will be noted that the thin film may also be peeled off by subjecting the substrate after the thin film formation to ultrasonic treatment to physically erode the hydrophilic layer. This ultrasonic treatment should preferably be carried out under such conditions as to leave part of the hydrophilic layer on the thin film surface.

Specific example of microbead fabrication method I (Case of providing a hydrophilic layer as a sacrificial layer)

Hydrophilic Layer-Forming Step to Forming Step

Figure 3:
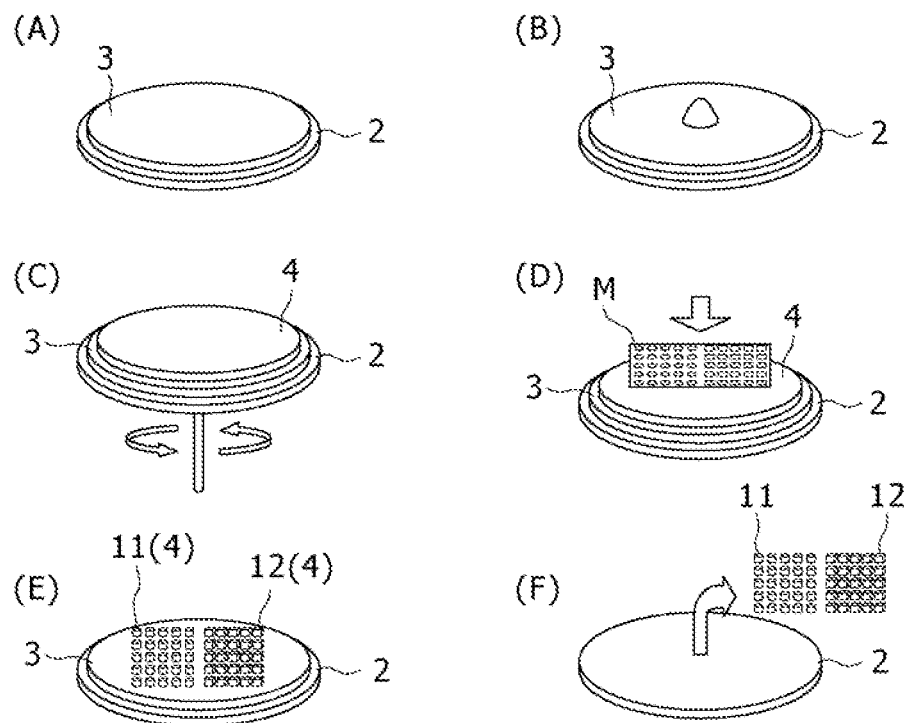
FIG. 3 is a perspective view schematically showing a configuration on a substrate in film-forming step $S_1$ to forming step $S_3$ and peeling-off step $S_7$ of the microbead fabrication method according to the first example embodiment of the disclosure.
Figure 4:
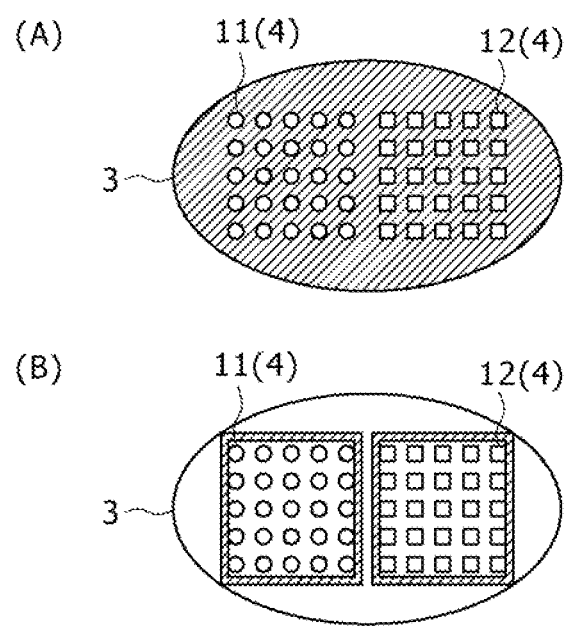
FIG. 4 is a top plan view schematically showing a configuration on a substrate in a water repellent finishing step $S_4$ of the microbead fabrication method according to the first example embodiment of the disclosure.
Figure 5:
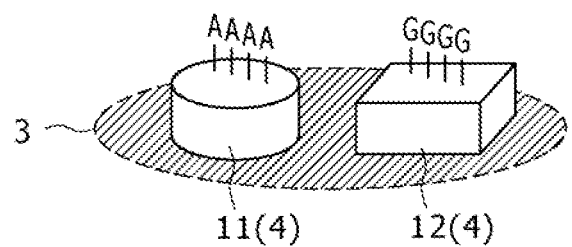
FIG. 5 is a perspective view schematically showing a configuration on a substrate in a solid-phasing step $S_6$ of the microbead fabrication method according to the disclosure.
Figure 5:
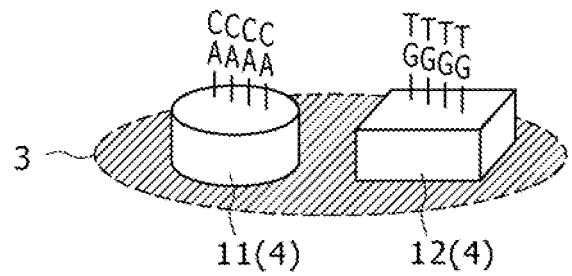

Next, with reference to FIGS. 3 to 5, methods of fabricating microbeads and a bead set according to the first example embodiment are particularly described. FIG. 3 is a perspective view schematically showing a configuration on a substrate in film-forming step $S_1$ to forming step $S_3$ and peeling-off step $S_7$. SU-8 is used herein as a microbead material and an example of the case where microbeads and a microbead set shown in FIG. 1 are fabricated is described.

Initially, in the film-forming step $S_1$, a hydrophilic layer 3 is laminated on a substrate 2 (see (A) of FIG. 3). Next, in the film-forming step $S_2$, SU-8 is placed on the hydrophilic layer 3 (see (B) of FIG. 3), followed by spin coating to form a thin film 4 (see (C) of FIG. 3).

At this stage, the amount of SU-8 and the rotation frequency of a spin coater (see the arrows in the figure) are controlled to control a thickness of the thin film 4, thereby appropriately setting a thickness of microbeads to be fabricated (see symbol h in FIG. 1).

The thin film 4 formed in the film-forming step $S_1$ is prebaked, followed by exposure to light by use of mask M drawn with a configuration of microbeads in the forming step $S_3$ (see (D) of FIG. 3). The arrow in the figure indicates light from a light source.

The exposed substrate 2 is immersed in a liquid developer to remove the thin film 4 at unnecessary portions thereof. Moreover, the substrate is rinsed with a liquid rinse agent, so that microbeads 11, 12 appear in the form of thin films 4 left on the substrate 2 (see (E) of FIG. 3).

When the configuration in the mask M is designed depending on the configuration of microbeads to be fabricated, microbeads having an arbitrary configuration can be formed on the substrate 2. Likewise, if the mask M is designed arbitrarily, microbeads having different configurations can be formed in arbitrary numbers, respectively. Thus, according to the microbead fabrication method of the example embodiment, microbeads of the types that are discriminable depending on the difference in configuration can be efficiently fabricated at low costs. In addition, depending on the design of mask, a bead set wherein populations of a number of types of microbeads are distinctly set can be fabricated.

Functional Group Modification Step to Water Repellent Finishing Step

In the microbead fabrication method of this example embodiment, the functional group modification is made on the surface of the thin films 4 at portions serving as the microbeads 11, 12 in the functional group modification step $S_4$. In the water repellent finishing step $S_5$, the regions of the substrate 2, from which the thin film 4 has been removed (i.e. substrate regions among the thin films 4 at portions serving as the microbeads 11, 12), are subjected to water repellent finish. Thereafter, a nucleic acid or a peptide or the like is solid-phased on the respective thin film surfaces in the solid-phasing step $S_6$.

FIG. 4 is a top plan view schematically showing a configuration on a substrate in the water repellent finishing step $S_5$.

(A) of FIG. 4 indicates the case where the microbeads 11, 12 are formed on the substrate 2 as illustrated in FIG. 3. The thin films 4 only at portions serving as the microbeads 11, 12 are left on the substrate according to the forming step $S_3$ and the other portions are removed (see (E) of FIG. 3). In the water repellent finishing step $S_5$, water repellency is imparted to the substrate regions, which are indicated by hatched lines and from which the thin film 4 has been removed, (i.e. regions wherein the hydrophilic layer 3 is exposed). The water repellent finish is carried out, for example, by subjecting the substrate regions, indicated by the hatched lines, to triethoxy-1H,1H,2H,2H-tridecafluoro-n-octylsilane treatment.

This enables the solutions dropped on the surfaces of the thin films 4 at portions serving as microbeads 11, 12 to be prevented from mutual mixing. Accordingly, in the solid-phasing step $S_6$, when a monomer solution or a preliminarily synthesized nucleic acid or peptide solution is dropped on a thin film surface at a portion serving as a microbead, such a solution can be reliably spotted at an aimed site and thus, a nucleic acid chain or the like having a desired base sequence or amino acid sequence can be synthesized and solid-phased. In addition, when a sugar chain and a compound are solid-phased, no mixing thereof occurs.

In (A) of FIG. 4, the water repellent finish is carried out so as to surround the respective thin film portions serving as microbeads. In case where a plurality of microbeads of the same type are formed on a substrate, water repellent finish may be carried out so as to surround a region on which microbeads of the same type are formed. For instance, where two types of microbeads 11, 12 are, respectively, formed in given numbers, water repellent finish is carried out at the hatched regions indicated in (B) of FIG. 4. This enables a monomer solution or the like to be dropped collectively for the same type of microbeads (a group of microbeads) and a solution dropped on other adjacent group of microbeads to be prevented from mixing.

The monomer solution or the like is dropped by spotting with a pipette or a microdispenser or by inkjet spotting. When using such a spotting system, microdroplets having minutely different liquid physical properties and relatively high viscosities are discharged in air and deposited on the substrate. When discharged, spray-like droplets (so-called "satellite") generate, so that a monomer solution or the like has happened to be deposited on sites other than intended ones.

In the microbead fabrication method of the disclosure, since microbeads are finally peeled off from a substrate, no problem is involved if such a monomer solution or the like is deposited, in the form of satellite, on substrate regions other than the portions serving as microbeads.

Solid-Phasing Step

FIG. 5 is a perspective view schematically showing a configuration on a substrate in the solid-phasing step $S_6$. An instance is illustrated herein, in which as shown in FIG. 3 and (A) of FIG. 4, the microbeads 11, 12 are formed on the substrate 2 and subjected to water repellent treatment, followed by solid-phasing a nucleic acid on the surfaces of the microbeads 11, 12 through step synthesis. In the figure, the microbeads 11, 12 formed on the upper layer of the hydrophilic layer 3 are shown as enlarged.

First, a monomer solution containing adenine "A" is dropped on the surface of the thin film 4 at portions serving as the microbeads 11. A linker is introduced to the surface of the thin film 4 in the functional group modification step $S_4$. Likewise, a monomer solution containing guanine "G" is dropped on the surface of the thin film 4 at portions serving as the microbeads 12. Thereafter, the binding reaction with adenine or guanine in the dropped monomer solution is carried out (see (A) of FIG. 5).

Secondly, a monomer solution containing cytosine "C" is dropped at a portion serving as the microbead 11 and a monomer solution containing thymine "T" is dropped on a portion serving as the microbead 12, followed by second-stage binding reactions (see (B) of FIG. 5). Hereinafter, the synthetic step is repeated until desired base sequences are obtained.

In the water repellent finishing step $S_5$, the water repellent finish is carried out over the region indicated by the hatched portion in the figure, for which the monomer solution dropped on the portion serving as the microbead 11 and monomer solution dropped on the portion serving as the microbead 12 are not mixed with each other. Thus, a nucleic acid chain having a desired base sequence can be accurately synthesized and solid-phased on the surface of the respective microbeads 11, 12.

With the solid-phasing based on such a photochemical reaction as used for known DNA chips, four binding reactions using four photomasks for the respective bases (A, G, T and C) have to be carried out for one-stage reaction. In contrast thereto, according to the disclosure, monomer solutions containing the respective bases are, respectively, dropped on the microbeads separated with the water-repellent finished region thereby performing the binding reactions simultaneously. Thus, the synthesis and solid-phasing of nucleic acid chains can be carried out at low costs.

Peeling-Off Step

Figure 6:
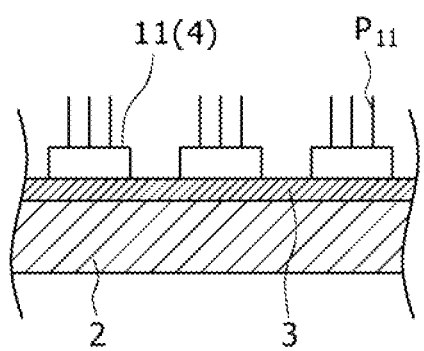
FIG. 6 is a sectional view schematically showing substrate (A) after the film-forming step $S_1$ to solid-phasing step $S_6$ and substrate (B) after the peeling-off step $S_7$ of the microbead fabrication method according to the first example embodiment of the disclosure.
Figure 6:
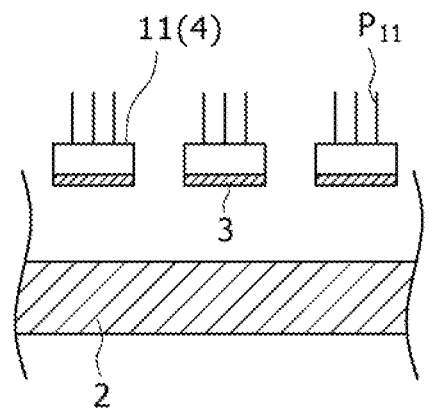

FIG. 6 is a sectional view schematically showing (A) a substrate obtained after completion of the film-forming step $S_1$ to solid-phasing step $S_6$ and (B) a substrate obtained after further completion of the peeling-off step $S_7$. The figure shows a section of a region on the substrate 2 on which the microbeads 11 have been formed.

On the substrate 2 after completion of the film-forming step $S_1$ to solid-phasing step $S_6$, the thin films 4 (microbeads 11), which are solid-phased with a nucleic acid or the like $P_{11}$ on the surface thereof, are laminated through the hydrophilic layer 3 according to photolithography.

In the peeling-off step $S_7$, the hydrophilic layer 3 functioned as a so-called sacrificial layer is partially dissolved in a solvent set at a temperature at which re-dissolution is possible, or the substrate 2 is subjected to ultrasonic treatment, thereby permitting the microbeads 11 (thin films 4) to be peeled off from the substrate 2 (see (B) of FIG. 6). In this way, there can be obtained the microbeads 11, 12 and a bead set 1 constituted thereof as shown in (F) of FIG. 3.

The thus obtained microbeads 11 has a steric configuration having two substantially parallel opposing faces ascribed to the afore-described fabrication process. More particularly, the two substantially parallel opposing faces are formed as a result of the film-forming step $S_2$ of the thin film 4. The distance between the two faces corresponds to a thickness of the microbead (see symbol h in FIG. 1) and can be arbitrarily controlled by controlling the film thickness.

The nucleic acid or the like $P_{11}$ is solid-phased on one of the two substantially parallel opposing faces of the microbead 11. The other face (the surface at the side contacting the hydrophilic layer 3) is imparted with hydrophilicity ascribed to the hydrophilic layer 3, part of which is left as not dissolved.

Microbead Fabrication Method II
Case of Providing a Sacrificial Layer Separately from a Hydrophilic Layer)

Figure 7:
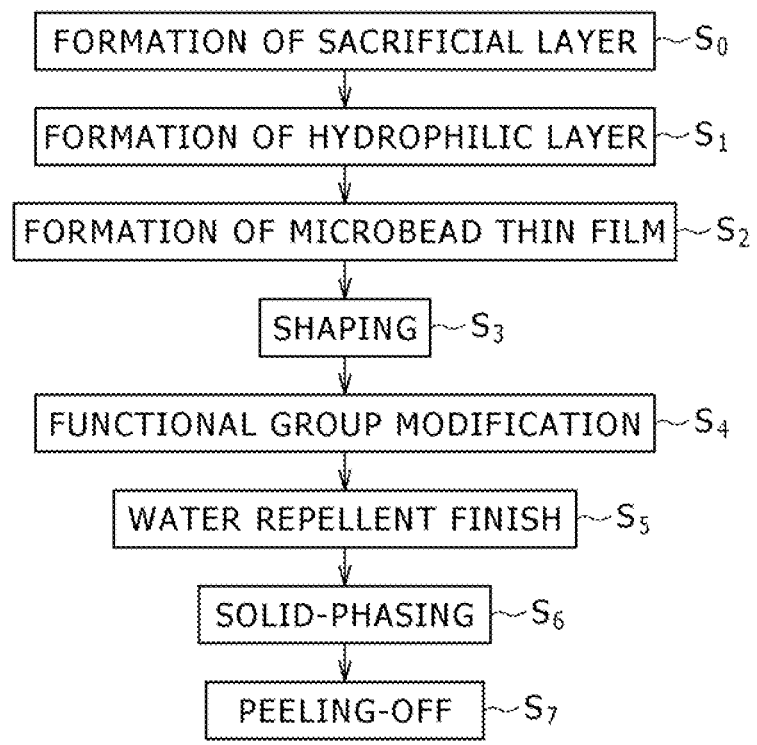
FIG. 7 is a flow chart showing the steps of a microbead fabrication method according to a second example embodiment of the disclosure.

FIG. 7 is a flow chart showing the steps of a microbead fabrication method according to a second example embodiment.

In the microbead fabrication method related to the first example embodiment, the hydrophilic layer formed in the step $S_1$ has a function as a so-called sacrificial layer. The microbead are peeled off and simultaneously imparted with hydrophilicity on the surface thereof by eroding the hydrophilic layer while leaving part thereof on the thin film surface in the peeling-off step $S_7$. In this case, it is necessary that the hydrophilic layer be eroded under such conditions as to leave part of the hydrophilic layer on the thin film surface so as to impart satisfactory hydrophilicity to the bead surface.

The microbead fabrication method according to the second example embodiment illustrated herein is characterized in that prior to the formation of the hydrophilic layer, a "sacrificial layer" functioning to permit microbeads to be peeled off in place thereof is separately formed. Accordingly, in the microbead fabrication method of this second example embodiment, the hydrophilic layer functions to impart hydrophilicity only at the bottom face of the microbead.

Sacrificial Layer-Forming Step

In "sacrificial layer-forming step" indicated by symbol $S_0$ in FIG. 7, a sacrificial layer is formed on a substrate by use of a fluorine-based organic material or polyimide organic material, or a hydrophilic organic material of the same or different type as for the hydrophilic layer.

Case where a Sacrificial Layer Formed by Use of a Fluorine-Based Organic Material Where the sacrificial layer is formed of a fluorine-based organic material, there is used a fluorine derivative such as a triazine used as a low molecular weight material, a condensed aromatic fluorine derivative or a fluorine derivative such as adamantine. As a fluorine-based organic material in the form of a polymer material, mention is made of fluorine resins such as fully fluorinated resins, partially fluorinated resins, fluorine-containing photocurable resins and the like. The fluorine-based organic material is dissolved in a solvent and formed into a film by spin coating, dried or photocured to provide a film.

Since fluorine-based organic materials become more sparingly soluble in water or organic solvents at a higher degree of fluorination, they become soluble only in fluorine-based solvents. Accordingly, if the sacrificial layer is formed of a fluorine-based organic material, such a sacrificial layer undergoes no erosion or damage with chemicals employed in the bead fabrication steps prior to the peeling-off step and the step of solid-phasing a nucleic acid or the like.

Further, fluorine-based solvents are unlikely to mix with charge-bearing polymers and have the capability of sparingly dissolving polymers other than fluorine-based polymers. In this sense, when a layer of a fluorine-based organic material is provided as the sacrificial layer and is eroded with a fluorine-based solvent in the peeling-off step $S_7$, the nucleic acid or the like solid-phased on the microbeads does not undergo denaturation, damage, release and the like thereof. Moreover, when a low molecular weight material such as a fluorine derivative of a triazine is used especially as the fluorine-based organic material, the microbeads can be peeled off through sublimation of the sacrificial layer in the peeling-off step $S_7$, ensuring more reliably keeping the interactivity of the nucleic acid or the like with a target nucleic acid or target protein.

A preferred degree of fluorination of the fluorine-based organic material is at not less than about 30% by atom %. The degree of fluorination set within this numerical range enables a sacrificial layer to be obtained as provided with a dissolution resistance to a solvent, such as cyclopentanone, 1-methoxy-2-propylacetate or the like, used, for example, in the film-forming step $S_2$.

Case of Forming a Sacrificial Layer by Use of a Polyimide Organic Material

Where the sacrificial layer is formed of a polyimide organic material, general-purpose polyimide resins are used. If the sacrificial layer is formed of a polyimide organic material, the sacrificial layer does not undergo erosion and damage by means of chemicals employed in the bead fabrication steps prior to the peeling-off step and also in the solid-phasing step of a nucleic acid or the like. Moreover, if the layer is eroded with an aprotic solvent, such as N-methyl-2-pyrrolidone or the like, in the peeling-off step $S_7$, the nucleic acid or the like solid-phased on the microbeads does not undergo denaturation, damage, release and the like. It will be noted that the sacrificial layer may be formed of a novolac resin in place of the polyimide resin.

Case of Forming a Sacrificial Layer by Use of a Hydrophilic Organic Material

Where the sacrificial layer is formed by use of a hydrophilic organic material, there is used a hydrophilic organic material of the same or different type as used for a hydrophilic layer described hereinafter. In the microbead fabrication method according to this second example embodiment, the material for hydrophilic layer used is one or more of hydrophilic organic materials selected from photosensitive hydrophilic resins, polyvinyl alcohol, starch, dextrin, amylose, gelatin, agar, carageenan, pectin and locust bean gum.

Although the sacrificial layer may be formed by use of a hydrophilic organic material of the same type as these hydrophilic layer materials, it is preferred to use a material that is different in type from the hydrophilic organic material of the hydrophilic layer and is high in re-dissolubility. The reason for this is as follows.

That is, the sacrificial layer formed of a hydrophilic organic material is dissolved by use of a solvent set at a temperature (e.g. approximately 45° C. or over), at which the hydrophilic organic material for the sacrificial layer can be re-dissolved in the peeling-off step $S_7$. At the time, in order that a hydrophilic layer formed in the film-forming step $S_1$ is not dissolved, the sacrificial layer is preferably formed of a material that is more likely to be re-dissolved than the hydrophilic layer.

More particularly, it is preferred that a photosensitive hydrophilic resin or polyvinyl alcohol is used as the material for the hydrophilic layer, and a material for the sacrificial layer makes use of a hydrophilic organic material other than the first-mentioned material. The photosensitive hydrophilic resin is gelled and becomes insoluble in cold water when photosensitized. When polyvinyl alcohol is dissolved in a heated solvent, coated onto a substrate and dried, it is not re-dissolved unless heated again. Accordingly, if the hydrophilic layer is formed of a photosensitive hydrophilic resin or polyvinyl alcohol and the sacrificial layer is formed of other type of hydrophilic organic material, only the sacrificial layer can be eroded while preserving the hydrophilic layer. It is to be noted that in case where the hydrophilic layer is physically eroded by ultrasonic treatment to peel off the thin film, it is preferred for the same reason that the sacrificial layer is formed of a hydrophilic organic material that differs in type from the hydrophilic layer and is more likely to be eroded by ultrasonic treatment.

Film-Forming Step to Solid-Phasing Step of a Hydrophilic Layer

"Hydrophilic layer-forming step" indicated by symbol $S_1$ in FIG. 7 is a step of forming a hydrophilic layer laminated on the sacrificial layer formed on the substrate. This step $S_1$ may be carried out in the same manner as in the microbead fabrication method according to the first example embodiment except that the hydrophilic layer is laminated on the sacrificial layer.

In this regard, however, attention should be paid to the fact that the hydrophilic layer formed in the step $S_1$ of the second example embodiment does not function as a sacrificial layer, but only to impart hydrophilicity to the microbead surface.

The materials for the hydrophilic layer include one or more of hydrophilic organic materials selected from photosensitive hydrophilic resins, polyvinyl alcohol, starch, dextrin, amylose, gelatin, agar, carageenan, pectin and locust bean gum. Of these, it is preferred that the hydrophilic layer is formed of a photosensitive hydrophilic resin or polyvinyl alcohol whose re-dissolubility is low for the purpose of eroding the sacrificial layer alone while preserving the hydrophilic layer in the peeling-off step $S_7$.

For the photosensitive hydrophilic resin, there may be used a water-soluble photosensitive resin wherein an azido-based photosensitive group is pendant from polyvinyl alcohol, for example. The film formation of a photosensitive hydrophilic resin is carried out by coating a resin, dissolved in a solvent, onto a substrate such as by spin coating or the like and subjecting to photosensitization.

The photosensitization of a photosensitive hydrophilic resin is carried out in the same photosensitive wavelength region and exposure energy as for a thin film material subjected to film formation in the succeeding film-forming step $S_2$ of a microbead thin film, for which there can be used a photosensitive hydrophilic resin whose positive and negative attributes are the same. In this case, when a formed thin film is formed in desired configurations by photolithography in the forming step $S_3$, the hydrophilic layer can be photosensitized by use of the same mask. Thus, a working efficiency can be enhanced by exposing the hydrophilic layer made of a photosensitive hydrophilic resin and a microbead thin film by use of the same mask at one time. Only portions of the hydrophilic layer in contact with the thin films formed as microbeads can be subjected to crosslinkage, bringing about enhanced adhesion of the hydrophilic layer to the thin films serving as microbeads. It will be noted that exposures to the hydrophilic layer and microbead thin films may, of course, be carried out by use of separate masks.

The photosensitized photosensitive hydrophilic resin becomes insolubilized in cold water by gelation. An uncured photosensitive resin can be removed by dissolving in hot water set at 35° C. or over.

The steps other than those illustrated herein and including the microbead thin film-forming step $S_2$, forming step $S_3$, functional group modification step $S_4$, water repellent finishing step $S_5$ and solid-phasing step $S_6$ can be performed in the same way as in the microbead fabrication method according to the first example embodiment. Hence, illustration of these steps is omitted herein.

Peeling-Off Step

Erosion of a Sacrificial Layer

"Peeling-off step" indicated by symbol $S_7$ in FIG. 7 is a step of peeling off a post-shaped thin film, solid-phased with a nucleic acid or peptide, from a substrate.

Figure 8:
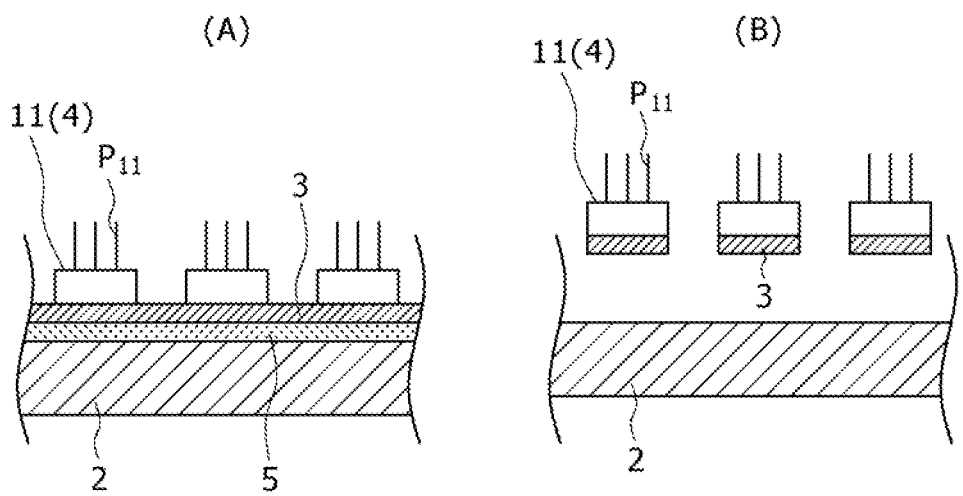
FIG. 8 is a sectional view schematically showing substrate (A) after a film-forming step $S_0$ to solid-phasing step $S_6$ and substrate (B) after the peeling-off step $S_7$ of the microbead fabrication method according to the second example embodiment of the disclosure.

FIG. 8 is a sectional view schematically showing (A) a substrate obtained after film-forming step $S_0$ to solid-phasing step $S_6$ are carried out and (B) a substrate obtained after a peeling-off step $S_7$ is further carried out. The figures, respectively, show a section of a region over a substrate 2 formed thereon with microbeads 11.

As shown in (A) of FIG. 8, in the microbead fabrication method of this example embodiment, a sacrificial layer 5 is formed (step $S_0$) as a sacrificial layer, on which a hydrophilic layer 3 (step $S_1$) and microbead thin films 4 (step $S_2$) are laminated. In this peeling-off step $S_7$, the sacrificial layer 5 is physically or chemically eroded to peel off the thin films 4 along with the hydrophilic layer 3 to obtain microbeads 11.

More specifically, where the sacrificial layer 5 is formed of a fluorine-based organic material, a fluorine-based solvent is used as a liquid remover to erode the sacrificial layer 5, or the fluorine-based organic material is sublimated to erode the sacrificial layer 5. The fluorine-based solvent is unlikely to mix with charge-bearing polymers and has such properties of sparingly dissolving polymers. Accordingly, if a fluorine-based solvent is used to erode the sacrificial layer 5, the sacrificial layer 5 alone can be eroded without re-dissolving the hydrophilic layer 3. When a low molecular weight material, particularly, a fluorine derivative of a triazine, is used as a fluorine-based organic material layer, sublimation and removal at low temperatures of 100° C. or below can be made, with the hydrophilic layer being not damaged.

Where the sacrificial layer 5 is formed of a polyimide organic material, an aprotic solvent is used as a liquid remover to erode the sacrificial layer 5 therewith.

Upon erosion of the sacrificial layer 5 formed of a fluorine-based organic material or polyimide organic material, the layer is removed by complete dissolution or sublimation so as not to allow it to be left on the surface of the peeled-off microbeads 11. If the sacrificial layer 5 is left on the microbead surface, there is some possibility that the resulting microbeads mutually coagulate owing to the hydrophobicity of the fluorine-based organic material or polyimide organic material.

Where the sacrificial layer 5 is formed of a hydrophilic organic material, the sacrificial layer 5 is eroded with a solvent set at a temperature, at which the hydrophilic organic material can be re-dissolved, or by ultrasonic treatment. In this case, the sacrificial layer 5 should preferably be formed of a hydrophilic organic material, which is different in type from that of the hydrophilic layer 3 and is more likely to be eroded. This makes it possible to erode the sacrificial layer alone by ultrasonic treatment or hot water treatment while preserving the hydrophilic layer 3 as it is.

In case where the sacrificial layer 5 is formed of a hydrophilic organic material, the hydrophilicity on the bead surface based on the hydrophilic layer 3 does not lower even if the sacrificial layer 5 being eroded is left on the surface of the microbeads 11 without complete dissolution thereof.

Etching of the Hydrophilic Layer

Prior to the erosion of the sacrificial layer 5, it is preferred to etch the hydrophilic layer 3. The thin film 4 formed on the substrate in the film-forming step $S_2$ is processed in the forming step $S_3$ in such a way that only portions serving as the microbeads 11 are left and the other portions are removed. The hydrophilic layer 3 exposed in the substrate region (substrate regions among the formed thin films), from which the thin film 4 has been removed, is removed by etching. This facilitates the sacrificial layer 5 located at positions beneath the hydrophilic layer 3 to be dissolved or sublimated.

Etching is carried out by use, as a liquid remover, of a solvent set at a temperature, at which the hydrophilic organic material can be re-dissolved and is carried out under such conditions that the hydrophilic layer 3 exposed among the post-shaped thin films 4 (microbeads 11) can be dissolved and removed. The etching conditions should be ones, under which the microbeads 11 are not peeled off by excess dissolution of the hydrophilic layer 3.

In this regard, where the hydrophilic layer 3 is formed of a photosensitive hydrophilic resin, an uncured photosensitive hydrophilic resin alone exposed among the post-formed thin films 4 (microbeads 11) can be selectively removed, so that the peeling-off of the microbeads can be effectively prevented.

In the microbead fabrication method of the second example embodiment, the sacrificial layer 5 is eroded in the peeling-off step $S_7$, with the result that while most of the hydrophilic layer 3 is left on the surface at a side contacting the hydrophilic layer 3 of the thin film 4, the post-formed thin films 4 (microbeads 11) can be peeled off.

Especially, as having illustrated hereinbefore, where the hydrophilic layer 3 is formed of a photosensitive hydrophilic resin whose negative and positive attributes are same by the same photosensitive wavelength region and exposure energy as the thin film 4 and the hydrophilic layer and the microbead thin film are subjected to light exposure by use of the same mask, the adhesion between the post-formed thin films 4 (microbeads 11) and the hydrophilic layer contacting therewith is enhanced. Thus, the microbeads can be peeled off in such a state that all the hydrophilic layer 3 is preserved as it is.

In this way, the microbead fabrication method of this example embodiment is able to impart better hydrophilicity to the microbead surface than the method of the previously illustrated second example embodiment.

Example 1

1. Fabrication of Microbeads Wherein a Hydrophilic Layer (PVA) is Functioned as a Sacrificial Layer In this example, SU-8 formed as a film on a substrate was formed by photolithography and subjected to solid-phasing of a nucleic acid chain, followed by peeling off to obtain microbeads. A hydrophilic layer was formed herein by use of polyvinyl alcohol (PVA), which was functioned as a so-called sacrificial layer thereby permitting the SU-8 thin film to be peeled off.

(1) Hydrophilic Layer-Forming Step

PVA (a full saponification type with a degree of polymerization of 500, made by Wako Pure Chemical Industries, Ltd., and used after controlled by thermal dissolution to 10 wt %) was spin coated (while keeping initially at 500 r.p.m., for five seconds and then at 2500 r.p.m., for 30 seconds) onto a silicon substrate, subjected to $O_2$-plasma treatment (direct plasma, gas species: $O_2$, power: 100 W, flow rate: 30 sccm, and time: 10 seconds), followed by drying at 85° C. for 120 minutes. The measurement of a PVA film thickness with a contact film thickness meter revealed a thickness of about 600 nm.

(2) Microbead Thin Film-Forming Step

In order to ensure adhesion between the PVA and SU-8, the PVA-coated substrate was subjected to $O_2$-plasma treatment (direct plasma, gas species: $O_2$, power: 100 W, flow rate: 30 sccm and time: 10 seconds) and activated, followed by spin coating (while keeping initially at 500 r.p.m., for five seconds and then at 5000 r.p.m., for 30 seconds) with 2-(3,4-epoxycyclohexyl)ethyltrimethoxysilane (made by Tokyo Chemical Industry Co., Ltd.) diluted to 30 wt % with toluene and drying at 100° C. for 90 seconds.

SU-8 (SU-8-3035-N-02, made by Kayaku Microchem Corporation, and used after doubling dilution with cyclopentanone) was spin coated (while keeping initially at 500 r.p.m., for 15 seconds and then at 1500 r.p.m., for 30 seconds) and dried at 100° C. for two minutes.

(3) Forming Step

Using a chromium mask having a bead pattern drawn therein, i-ray exposure (170 mJ/cm$^2$) with a contact aligner was carried out, followed by drying at 100° C. for three minutes. Development with a SU-8 developer (made by Kayaku Microchem Corporation) was made and after rinsing with IPA, hard baking at 150° C. for 10 minutes was performed to obtain an aligned bead pattern on the substrate. The measurement of the SU-8 film thickness with a contact film thickness meter revealed a thickness of about 3 μm.

(4) Functional Group Modification Step

The SU-8 bead pattern-bearing substrate was subjected to $O_2$-plasma treatment (direct plasma, gas species: $O_2$, power: 100 W, flow rate: 30 sccm and time: 10 seconds) and activated, followed by treatment with 2-(3,4-epoxycyclohexyl)ethyltrimethoxysilane (120° C., 10 hours, gas phase reaction).

(5) Solid-Phasing Step

Oligo DNA-1 (see sequence No. 1 in Table 1) indicated in (A) of FIG. 9 was dissolved in a 2×SSC buffer to make a 10 μM thereof and the silane-coupled bead-bearing substrate was infiltrated under agitation for 12 hours. The substrate was removed and rinsed under agitation in a 2×SSC buffer containing 0.2 M of SDS for 15 minutes. Next, the substrate was rinsed under agitation for five minutes in a fresh 2×SSC buffer containing 0.2 M of SDS while heating to 90° C. The substrate was rinsed with running water for three minutes and dried.

TABLE 1

| Oligo DNA-1 | 5'-GACAATGTGTACATC AACATCACCTACCAC-3' | (Sequence No. 1) |
| Oligo DNA-2 | 5'-GACAATGTGTACATC AACATCACCTACCAC-3' | (Sequence No. 2) |
| Oligo DNA-3 | 5'-GTGGTAGGTGATGTT GATGTACACATTGTC-3' | (Sequence No. 3) |

Here, a red fluorescence derived from cyanine dye Cy3 was observed through a fluorescent microscope, confirming that the oligo DNA-1 was solid-phased on the SU-8 beads.

(6) Peeling-Off Step

The silicon substrate whose beads were in pattern was immersed in a cold water bath, followed by gradually raising the temperature to 45° C. and discarding the water. Next, cold water and toluene were added and the bath temperature was raised to 65° C., and the peeled-off beads were subjected to thermal filtration, followed by rinsing with hot water and drying.

Thereafter, the resulting microbeads were observed through a fluorescent microscope, revealing a red fluorescence derived from the cyanine dye Cy3. The fluorescent intensity of the microbeads underwent no change when compared with the fluorescent intensity of the SU-8 beads prior to the peeling-off step, revealing that the oligo DNA-1 underwent no denaturation, release or the like in this peeling-off step.

Example 2

2. Microbead Fabrication Wherein a Hydrophilic Layer (Starch) was Functioned as a Sacrificial Layer In this example, starch was used to form a hydrophilic layer and this layer was functioned as a so-called sacrificial layer to permit SU-8 thin films to be peeled off (1) Hydrophilic Layer-Forming Step Starch (derived from corn, made by Wako Pure Chemical Industries, Ltd., and prepared by thermal dissolution to 4 wt %) was spin coated (while keeping initially at 500 r.p.m., for five seconds and then at 2500 r.p.m., for 30 seconds) onto a silicon substrate, subjected to $O_2$-plasma treatment (direct plasma, gas species: $O_2$, power: 100 W, flow rate: 30 sccm, and time: 10 seconds), followed by drying at 85° C. for 120 minutes. The measurement of a starch film thickness with a contact film thickness meter revealed a thickness of about 150 nm on average.

(2) Microbead Thin Film-Forming Step to Solid-Phasing Step

In the same manner as in Example 1, SU-8 was spin coated, subjected to patterning, development and activation by $O_2$-plasma treatment, followed by treatment with (3-glycidoxypropyl)triethoxysilane.

Similarly, oligo DNA-1 (see sequence No. 1 on "Table 1") indicated in (A) of FIG. 9 was solid-phased. A red fluorescence derived from cyanine dye Cy3 was observed through a fluorescent microscope, revealing that the oligo DNA-1 was solid-phased on the SU-8 beads.

(3) Peeling-Off Step

The silicon substrate wherein the beads were patterned was immersed in a cold water bath, followed by gradually raising the temperature to 45° C. and discarding the water. Next, cold water and toluene were added to the bath whose temperature was raised to 65° C., followed by thermal filtration of the peeled-off beads, rinsing with hot water and drying.

Thereafter, the resulting microbeads were observed through a fluorescent microscope and a red fluorescence derived from the cyanine dye Cy3 was confirmed. The fluorescent intensity of the microbeads underwent no change when compared with the fluorescent intensity of the SU-8 beads prior to the peeling-off step, revealing that the oligo DNA-1 underwent no denaturation, release or the like in this peeling-off step.

Example 3

3. Microbead Fabrication Wherein a Hydrophilic Layer (Agar) was Functioned as a Sacrificial Layer In this example, agar was used to form a hydrophilic layer and this layer was functioned as a so-called sacrificial layer to permit SU-8 thin films to be peeled off (1) Hydrophilic Layer-Forming Step Agar (Kanten Papa, made by Ina Food Industry Co., Ltd., and prepared by thermal dissolution to 8 wt %) was spin coated (while keeping initially at 500 r.p.m., for five seconds and then at 2500 r.p.m., for 30 seconds) onto a silicon substrate, subjected to $O_2$-plasma treatment (direct plasma, gas species: $O_2$, power: 100 W, flow rate: 30 sccm, and time: 10 seconds), followed by drying at 85° C. for 10 minutes. The measurement of an agar film thickness with a contact film thickness meter revealed a thickness of about 100 nm.

(2) Microbead Thin Film-Forming Step to Solid-Phasing Step

In the same manner as in Example 1, SU-8 was spin coated, subjected to patterning, development and activation by $O_2$-plasma treatment, followed by CVD treatment of 2-(3,4-epoxycyclohexyl)ethyltrimethoxysilane.

Similarly, oligo DNA-1 (see sequence No. 1 on "Table 1") indicated in (A) of FIG. 9 was solid-phased. A red fluorescence derived from cyanine dye Cy3 was observed through a fluorescent microscope, revealing that the oligo DNA-1 was solid-phased on the SU-8 beads.

(3) Peeling-Off Step

The silicon substrate wherein the beads were patterned was immersed in a cold water bath, followed by gradually raising the temperature to 45° C. and discarding the water. Next, cold water and toluene were added to the bath whose temperature was raised to 65° C., followed by thermal filtration of the peeled-off beads, rinsing with hot water and drying.

Thereafter, the resulting microbeads were observed through a fluorescent microscope and a red fluorescence derived from the cyanine dye Cy3 was confirmed. The fluorescent intensity of the microbeads underwent no change when compared with the fluorescent intensity of the SU-8 beads prior to the peeling-off step, revealing that the oligo DNA-1 underwent no denaturation, release or the like in this peeling-off step.

Example 4

4. Microbead Fabrication Wherein a Sacrificial Layer (Fluorine Resin) was Provided Separately from a Hydrophilic Layer (PVA)

In this example, a sacrificial layer was formed by use of an amorphous fluorine resin and was eroded to allow a SU-8 thin film to be peeled off thereby providing microbeads.

(1) Sacrificial Layer-Forming Step

Cytop (CTX-809AP2, made by Asahi Glass Co., Ltd., and used by diluting a stock solution to 80% with perfluorotributylamine) was spin coated (while keeping initially at 700 r.p.m., for three seconds and then at 4000 r.p.m., for 20 seconds) onto a silicon substrate, subjected to $O_2$-plasma treatment (direct plasma, gas species: $O_2$, power: 100 W, flow rate: 30 sccm, and time: 10 seconds), followed by drying at 50° C. for 30 minutes, then at 80° C. for 60 minutes and finally at 200° C. for 30 minutes. The measurement of a Cytop film thickness with a contact film thickness meter revealed a thickness of about 400 nm.

In order to improve the wettability of the Cytop and adhesion with PVA to be subsequently subjected to film formation, $O_2$—RIE treatment (gas species: $O_2$, power: 70 W, pressure: 18 Pa, flow rate: 10 sccm, and time: 15 seconds) and $O_2$-plasma treatment (direct plasma, gas species: $O_2$, power: 100 W, pressure: 3 Pa, flow rate: 30 sccm, and time: 15 seconds) were carried out.

(2) Hydrophilic Layer-Forming Step to Functional Group Modification Step

In the same manner as in Example 1, PVA was formed as a hydrophilic layer and 2-(3,4-epoxycyclohexyl)ethyltrimethoxysilane was spin coated, followed by spin coating of SU-8, patterning and development.

Likewise, the SU-8 bead pattern-bearing substrate was activated by subjecting to $O_2$-plasma treatment, followed by treatment with 2-(3,4-epoxycyclohexyl)ethyltrimethoxysilane (120° C., 10 hours, gas phase reaction).

(3) Solid-Phasing Step

Oligo DNA-2 (see sequence No. 2 of "Table 1") indicated in (B) of FIG. 9 was dissolved in a 2×SSC buffer to make a concentration of 10 μM, followed by infiltrating the silane-coupled bead-bearing substrate therewith under agitation for 12 hours. The substrate was removed and rinsed in a 2×SSC buffer containing 0.2 M of SDS under agitation for 15 minutes. Next, the substrate was rinsed in a 2×SSC buffer containing 0.2 M of SDS under agitation for five minutes while heating to 90° C. The substrate was rinsed with running water for three minutes and dried.

(4) Peeling-Off Step

The silicon substrate modified with the oligo DNA-2 was immersed in a cold bath and the temperature was gradually raised to 45° C. and kept for five minutes, followed by discarding the water and etching the hydrophilic layer.

The bead pattern-bearing silicone substrate was allowed to stand in a fluorine-based rinse agent (Novec HFE7300, made by Sumitomo 3M Limited) for 24 hours to permit the beads to be peeled off, followed by separation by filtration, rinsing with Novec HFE7300 set at a normal temperature and drying.

(5) Isolation of a Target Nucleic Acid Chain

Next, oligo DNA-3 (see sequence No. 3 in "Table 1") indicated in (C) of FIG. 9 was isolated and detected as a target nucleic acid chain.

The target nucleic acid chain oligo DNA-3 was adjusted to 2 μM (lx SSC aqueous solution) and mixed with the microbeads, on which the oligo DNA-2 had been solid-phased, under agitation at 50° C. for 12 hours. The beads were separated by filtration and rinsed in a 1×SSC buffer containing 0.2 M of SDS under agitation for 20 minutes. The beads were separated by filtration and dispersed over a slide glass and observed through a fluorescent microscope, thereby confirming a red fluorescence derived from cyanine dye Cy3.

Example 5

5. Microbead Fabrication Provided with a Sacrificial Layer (Polyimide Resist) Separately from a Hydrophilic Layer (PVA)

In this example, Omnicoat™ (made by Kayaku Microchem Corporation), which is an aliphatic polyimide resist, was used to form a sacrificial layer and was eroded to permit SU-8 thin films to be peeled off thereby making microbeads.

(1) Sacrificial Layer-Forming Step

Omnicoat (made by Kayaku Microchem Corporation) was spin coated (while keeping initially at 500 r.p.m., for five seconds and then at 3000 r.p.m., for 30 seconds) onto a silicon substrate, subjected to $O_2$-plasma treatment (direct plasma, gas species: $O_2$, power: 100 W, flow rate: 30 sccm, and time: 10 seconds), followed by drying at 200° C. for one minute.

In order to improve the wettability of the Omnicoat and also improve adhesion with PVA to be subsequently formed, $O_2$-plasma treatment (direct plasma, gas species: $O_2$, power: 100 W, flow rate: 30 sccm, and time: 10 seconds) was carried out for activation.

(2) Hydrophilic Layer-Forming Step to Forming Step

In the same manner as in Example 1, PVA was formed as a hydrophilic layer and 2-(3,4-epoxycyclohexyl)ethyltrimethoxysilane was spin coated, followed by spin coating of SU-8, patterning and development.

Here, exposure was effected using a mask wherein two different types of configurations were drawn and separated into two regions (hereinafter referred to as bead regions), each type having a plurality of configurations.

(3) Functional Group Modification Step

The bead-patterned silicon substrate was immersed in a cold water bath and the temperature was gradually raised to 45° C. and kept for five minutes, followed by discarding the water and etching the hydrophilic layer.

In the same manner as in Example 1, a SU-8 bead pattern-bearing substrate was activated by subjecting to $O_2$-plasma treatment, followed by CVD treatment of 2-(3,4-epoxycyclohexyl)ethyltrimethoxysilane. The substrate was immersed in a mixed solution of 800 ml of tetraethylene glycol and 3 ml of concentrated sulfuric acid and reacted at 80° C. for eight hours while agitating to cause the hydroxyl group modification to be carried out.

(4) At the stage of the water repellent finish, the two bead regions A, B were once covered with a resist and the other substrate regions were subjected to triethoxy-1H,1H,2H,2H-tridecafluoro-n-octylsilane treatment (120° C., 10 hours). The removal of the resist resulted in the impartment of water repellency to the substrate regions other than the bead regions A, B.

(5) In the bead regions A, B for the step syntheses of nucleic acids, the step syntheses of nucleic acids were carried out according to the base sequences indicted in "Table 2."

TABLE 2

| Bead region A | 5'-GAGAACGATC TTCAGGGTGC-3' | (Sequence No. 4) |
|---|---|---|
| Bead region B | 5'-CGATCTAGGT ACTGCAAGTA-3' | (Sequence No. 5) |

The respective nucleoside phosphoroamidites were prepared to make 0.1 M in propylene carbonate. Additionally, 5-ethylthiotetrazole was prepared to make 0.5 M in propylene carbonate.

The nucleoside phosphoramidite solutions were dropped on the bead regions by means of a pipette and the 5-ethylthiotetrazole solution was subsequently dropped in an equal amount by means of a pipette. The reaction was performed in an atmosphere of nitrogen for 60 seconds, rinsed with acetonitrile to remove excess reagents, and dried. Next, an oxidation solution (a 0.02 M iodine solution prepared with use of a mixed solution of pyridine/tetrahydrofuran/water) was dropped and reacted for 30 seconds thereby converting the resulting nucleoside phosphorous acid triester into nucleoside phosphoric acid triester. This followed by rinsing with acetonitrile, dropping a mixed solution of acetic acid anhydride/tetrahydrofuran, and reacting for 30 seconds to cause unreacted hydroxyl groups modified in the bead regions to be capped. After rinsing with acetonitrile and drying, a 2.5% dichloroacetic acid/dichloromethane solution was dropped and reacted for 60 seconds, thereby removing the dimethoxytrityl protecting group from the 5'-hdyroxyl group of the nucleoside.

After rinsing with acetonitrile and drying, the above steps of (a) nucleoside coupling, (b) rinsing with acetonitrile, (c) oxidation, (d) rinsing with acetonitrile, (e) dimethoxytrityl protection and (f) rinsing with acetonitrile were repeated 19 times. Finally, the substrate was immersed in a 13% ammonia/20% methylamine aqueous solution at room temperature for about one hour to de-protect the base moiety of the nucleic acid.

(6) Peeling-Off Step

The bead-patterned silicone substrate was infiltrated and agitated in N-methyl-2-pyrrolidone for 10 minutes, followed by separation of the beads by filtration, rinsing with ethanol and drying.

Example 6

6. Microbead Fabrication Provided with a Sacrificial Layer (PVA) Separately from a Hydrophilic Layer (Photosensitive Hydrophilic Resin)

In this example, a photosensitive hydrophilic resin was used to form a hydrophilic layer and PVA (GH-07) was used as a sacrificial layer, and a SU-8 thin film was peeled off to provide microbeads.

(1) Sacrificial Layer-Forming Step

GH-07 (Gosenol, partially saponified by 88%, made by Nihon Synthetic Chemical Co., Ltd., and used after thermal dissolution to 10 wt %) was spin coated (while keeping initially at 500 r.p.m., for five seconds and then at 2500 r.p.m., for 30 seconds) onto a silicon substrate subjected to $O_2$-plasma treatment (direct plasma, gas species: $O_2$, power: 100 W, flow rate: 30 sccm, time: 10 seconds), followed by drying at 85° C. for 120 minutes.

(2) Hydrophilic Layer-Forming Step

In order to improve adhesion between GH-07 and the photosensitive hydrophilic resin, $O_2$-plasma treatment (direct plasma, gas species: $O_2$, power: 100 W, flow rate: 30 sccm, time: 10 seconds) was carried out for activation. A photosensitive hydrophilic resin (Biosurfine AWP, made by Toyo Gosei Co., Ltd., and used by dilution to 3 wt % with water) was spin coated (while keeping initially at 350 r.p.m., for two seconds and then at 1000 r.p.m., for 30 seconds) and dried at 80° C. for five minutes. Next, in order to improve adhesion between the photosensitive hydrophilic resin and Su-8, 3-glycidyloxypropyltrimethoxysilane (diluted to 30 wt % with toluene) was spin coated (while keeping initially at 500 r.p.m., for five seconds, then at 4000 r.p.m., for 40 seconds and finally at 5000 r.p.m., for 30 seconds), followed by drying at 100° C. for two minutes.

(3) Microbead Thin Film-Forming Step to Solid-Phasing Step

In the same manner as in Example 1, SU-8 was spin coated, followed by i ray exposure (170 mJ/cm$^2$) by means of a contact aligner using a chromium mask in which a bead pattern was drawn, followed by drying at 100° C. for three minutes. Simultaneously with the exposure of the SU-8, the above AWP was cured. The SU-8 was developed with an SU-8 developer (made by Kayaku Microchem Corporation), followed by rinsing with IPA and developing the photosensitive hydrophilic resin with water set at 30° C. Hard baking was performed at 80° C. for 10 minutes, thereby obtaining a bead pattern aligned on the GH-07 layer. The measurement of the photosensitive hydrophilic resin film thickness with a contact film thickness meter revealed a thickness of about 200 nm. After activation by subjecting the SU-8 surface to $O_2$-plasma treatment, CVD treatment of 2-(3,4-epoxycyclohexyl)ethyltrimethoxysilane was carried out.

Similarly, oligo DNA-1 (see sequence No. 1 in "Table 1") indicated in (A) of FIG. 9 was solid-phased. The observation of a red fluorescence derived from cyanine dye Cy3 through a fluorescent microscope revealed that the oligo DNA-1 was solid-phased on the SU-8 beads.

(4) Peeling-Off Step

The bead-patterned silicon substrate was immersed in a cold water bath and the temperature was gradually raised to 45° C., followed by discarding the water. Next, cold water and toluene were added to the bath whose temperature was raised to 65° C., followed by thermal filtration of the peeled-off beads, rinsing with hot water and drying.

Thereafter, the resulting microbeads were observed through a fluorescent microscope, revealing a red fluorescence derived from cyanine dye Cy3. The fluorescent intensity of the microbeads underwent no change when compared with the fluorescent intensity of the SU-8 beads prior to the peeling-off step, revealing that the oligo DNA-1 were free of denaturation, release and the like in the peeling-off step.

Example 7

7. Microbead Fabrication Provided with a Sacrificial Layer (Fluorine Resin) Separately from a Hydrophilic Layer (Photosensitive Hydrophilic Resin)

In this example, a photosensitive hydrophilic resin was used to form a hydrophilic layer and an amorphous fluorine resin was used as a sacrificial layer, and SU-8 thin films were peeled off to provide microbeads.

(1) Sacrificial Layer-Forming Step

Cytop (CTX-809AP2, made by Asahi Glass Co., Ltd., and used by diluting a stock solution to 80% with perfluorotributylamine) was spin coated (while keeping initially at 700 r.p.m., for three seconds and then at 4000 r.p.m., for 20 seconds) onto a silicon substrate subjected to $O_2$-plasma treatment (direct plasma, gas species: $O_2$, power: 100 W, flow rate: 30 sccm, time: 10 seconds), followed by drying at 50° C. for 30 minutes, next at 80° C. for 60 minutes and finally at 200° C. for 30 minutes.'

In order to improve the wettability of the Cytop and also improve adhesion with a photosensitive hydrophilic resin to be subsequently formed as a film, $O_2$—RIE treatment was carried out in the same manner as in Example 4.

(2) Hydrophilic Layer-Forming Step

A photosensitive hydrophilic resin (Biosurfine AWP, made by Toyo Gosei Co., Ltd., and used by diluting to 3 wt % with water) was spin coated (while keeping initially at 350 r.p.m., for two seconds and then at 1000 r.p.m., for 30 seconds) and dried at 80° C. for five minutes. Next, 3-glycidyloxypropyltrimethoxysilane (diluted to 30 wt % with toluene) was spin coated (while keeping initially at 500 r.p.m., for five seconds, then at 4000 r.p.m., for 40 seconds and finally at 5000 r.p.m., for 30 seconds) and dried at 100° C. for two minutes.

(3) Microbead Thin Film-Forming Step to Solid-Phasing Step

In the same manner as in Example 1, SU-8 was spin coated and subjected to i ray exposure (170 mJ/cm$^2$) with a contact aligner using a chromium mask drawn with a bead pattern and dried at 100° C. for three minutes. Simultaneously with the SU-8 exposure, the above AWP was cured. The SU-8 was developed with an SU-8 developer (made by Kayaku Microchem Corporation) and rinsed with IPA, followed by development of the photosensitive hydrophilic resin with water set at 30° C. Hard baking was carried out at 80° C. for 10 minutes to obtain a bead pattern aligned on the Cytop layer. The SU-8 surface was activated by subjecting to $O_2$-plasma treatment, followed by CVD treatment of 2-(3,4-epoxycyclohexyl)ethyltrimethoxysilane.

Similarly, oligo DNA-1 (see sequence No. 1 in "Table 1") indicated in (A) of FIG. 9 was solid-phased. The observation of a red fluorescence derived from cyanine dye Cy3 through a fluorescent microscope revealed that the oligo DNA-1 was solid-phased on the SU-8 beads.

(4) Peeling-Off Step

The bead-patterned silicon substrate was allowed to stand for 24 hours in a fluorine-based rinse agent (Novec HFE 7300, made by Sumitomo 3M Limited) to permit the beads to be peeled off, followed by separation by filtration, rinsing with Novec HFE 7300 at a normal temperature and drying.

Thereafter, the resulting microbeads were observed through a fluorescent microscope, revealing the red fluorescent derived from the cyanine dye Cy3. The fluorescent intensity of the microbeads underwent no change on comparison with a fluorescent intensity of the SU-8 beads prior to the peeling-off step, confirming that the oligo DNA-1 underwent no denaturation, release or the like in this peeling-off step.

Example 8

8. Microbead Fabrication Wherein a Hydrophilic Layer (Photosensitive Hydrophilic Resin) was Functioned as a Sacrificial Layer In this example, a hydrophilic layer was formed by use of a photosensitive hydrophilic resin and also functioned as a so-called sacrificial layer to permit SU-8 thin films to be peeled off.

(1) Hydrophilic Layer-Forming Step

A photosensitive hydrophilic resin (Bisurfine AWP, made by Toyo Gosei Co., Ltd., and used by dilution to 3 wt % with water) was spin coated (while keeping initially at 350 r.p.m., for two seconds and then at 1000 r.p.m., for 30 seconds) and dried at 80° C. for five minutes. Next, 3-glycidyloxypropyltrimethoxysilane (diluted to 30 wt % with toluene) was spin coated (while keeping at 500 r.p.m., for five seconds, then at 4000 r.p.m., for 40 seconds and finally at 5000 r.p.m., for 30 seconds) and dried at 100° C. for two minutes.

(2) Microbead Thin Film-Forming Step to Solid-Phasing Step

In the same manner as in Example 1, SU-8 was spin coated, subjected to i ray exposure (170 mJ/cm$^2$) with a contact aligner using a chromium mask drawn with a bead pattern and dried at 100° C. for three minutes. The SU-8 was developed with an SU-8 developer (made by Kayaku Microchem Corporation) and rinsed with IPA, followed by development of the photosensitive hydrophilic resin with water set at 30° C. Hard baking was performed at 80° C. for 10 minutes to obtain a bead pattern aligned on the AWP layer. The SU-8 surface was activated by subjecting to $O_2$-plasma treatment, followed by CVD treatment of 2-(3,4-epoxycyclohexyl)ethyltrimethoxysilane.

Similarly, oligo DNA-1 (see sequence No. 1 in "Table 1") indicated in (A) of FIG. 9 was solid-phased. The observation of a red fluorescence derived from cyanine dye Cy3 through a fluorescent microscope revealed that the oligo DNA-1 was solid-phased on the SU-8 beads.

(3) Peeling-Off Step

The bead-patterned silicon substrate was placed in a water bath and subjected to ultrasonic treatment at 95° C. for 10 minutes, followed by separation of the resulting beads by filtration, rinsing with water at a normal temperature and then with IPA, and drying.

Thereafter, the resulting microbeads were observed through a fluorescent microscope, revealing the red fluorescent derived from the cyanine dye Cy3. The fluorescent intensity of the microbeads underwent no change in comparison with a fluorescent intensity of the SU-8 beads prior to the peeling-off step, confirming that the oligo DNA-1 underwent no denaturation, release or the like in this peeling-off step.

INDUSTRIAL APPLICABILITY

According to the microbead fabrication method of the disclosure, a bead set containing a variety of microbeads at given populations can be supplied. This bead set can be utilized in various biochemical analyses making use of microbeads. For instance, in a comprehensive comparison analysis of gene expression levels or protein expression levels, more reliable results of the comparison analysis are obtainable.

| Description of Reference Symbols | |
| --- | --- |
| 1: | Bead set |
| 11, 12: | Microbeads |
| 2: | Substrate |
| 3: | Hydrophilic layer |
| 4: | Thin film |
| 5: | Sacrificial layer |
| M: | Photomask (mask) |
| $P_{11}$, $P_{12}$: | Nucleic acid or the like |

The invention claimed is:

1. A method for fabricating microbeads comprising:
   (a) forming a hydrophilic layer made of a hydrophilic organic material on a substrate;
   (b) laminating, on the hydrophilic layer, a thin film capable of being peeled off as microbeads;
   (c) forming the thus formed thin film in a given configuration by photolithography;
   (d) solid-phasing a given substance on the post-formed thin film; and
   (e) peeling off the post-formed thin film, solid-phased with the substance, from the substrate along with at least a first part of the hydrophilic layer,
   wherein the at least a first part of the hydrophilic layer remains in contact with a surface of the post-formed thin film after the post-formed thin film has been peeled off from the substrate.

2. The method of claim 1, wherein the hydrophilic organic material dissolved in a solvent is coated onto the substrate and dried to form the hydrophilic layer, after which in the peeling-off step, a solvent set at a temperature, at which the hydrophilic organic material is able to be re-dissolved therein, is used to dissolve a second part of the hydrophilic layer, or ultrasonic treatment is effected to permit the post-formed thin film to be peeled off along with the at least a first part of the hydrophilic layer to obtain microbeads.

3. The method of claim 2, wherein the hydrophilic layer is formed by use of one or more of hydrophilic organic materials selected from polyvinyl alcohol, starch, dextrin, amylose, gelatin, agar, carageenan, pectin, locust bean gum and a photosensitive hydrophilic resin.

4. The method of claim 3, wherein the solid-phasing step is carried out by chemical synthesis of the substance on the thin film.

5. The method of claim 4, wherein one or more of biopolymers selected from nucleic acids or peptides having given sequences and sugar chains are solid-phased as the substance.

6. The method of claim 5, wherein regions among the post-formed thin films are subjected to water repellent finish after the forming step but prior to the solid-phasing step.

7. The method for of claim 6, wherein the thin films are formed by a photoresist or silicon dioxide.

8. The method of claim 1, which includes forming a sacrificial layer on the substrate, the hydrophilic layer being laminated on the sacrificial layer, after which the sacrificial layer is physically or chemically eroded in the peeling-off step to permit the post-formed thin film to be peeled off along with the hydrophilic layer to obtain microbeads.

9. The method of claim 8, wherein the hydrophilic layer is formed by use of one or more of hydrophilic organic materials selected from a photosensitive hydrophilic resin, polyvinyl alcohol, starch, dextrin, amylose, gelatin, agar, carageenan, pectin and locust bean gum.

10. The method of claim 9, wherein the sacrificial layer is formed by use of a fluorine-based organic material and the sacrificial layer formed of the fluorine-based organic material is sublimated or dissolved by use of a fluorine-based solvent in the peeling-off step whereby the post-formed thin films are allowed to be peeled off from the substrate along with the hydrophilic layer to obtain microbeads.

11. The method of claim 9, wherein the sacrificial layer is formed by use of a polyimide organic material and, in the peeling-off step, the sacrificial layer formed of the polyimide organic material is dissolved by use of an aprotic solvent to permit the post-formed thin films to be peeled off from the substrate along with the hydrophilic layer to obtain microbeads.

12. The method of claim 9, wherein the sacrificial layer is formed by use of a hydrophilic organic material of a type same as or different from the hydrophilic layer and the sacrificial layer formed of the hydrophilic organic material is dissolved by use of a solvent set at a temperature, at which the hydrophilic organic material is able to be re-dissolved therein, or is subjected to ultrasonic treatment in the peeling-off step to permit the post-formed thin films to be peeled off from the substrate along with the hydrophilic layer to obtain microbeads.

13. A method for fabricating microbeads comprising:
(a) forming a sacrificial layer on a substrate;
(b) laminating, on the sacrificial layer, a hydrophilic layer made of a hydrophilic organic material;
(b) laminating, on the hydrophilic layer, a thin film capable of being peeled off as microbeads;
(c) forming the thus formed thin film in a given configuration by photolithography;
(d) solid-phasing a given substance on the post-formed thin film; and
(e) peeling off the post-formed thin film, solid-phased with the substance, from the substrate along with the hydrophilic layer,
wherein the sacrificial layer is physically or chemically eroded in the peeling-off step to permit the post-formed thin film to be peeled off along with the hydrophilic layer to obtain microbeads.

14. The method of claim 13, wherein the hydrophilic layer is formed by use of one or more of hydrophilic organic materials selected from a photosensitive hydrophilic resin, polyvinyl alcohol, starch, dextrin, amylose, gelatin, agar, carageenan, pectin and locust bean gum.

15. The method of claim 13, wherein the sacrificial layer is formed by use of a fluorine-based organic material and the sacrificial layer formed of the fluorine-based organic material is sublimated or dissolved by use of a fluorine-based solvent in the peeling-off step whereby the post-formed thin films are allowed to be peeled off from the substrate along with the hydrophilic layer to obtain microbeads.

16. The method of claim 13, wherein the sacrificial layer is formed by use of a polyimide organic material and, in the peeling-off step, the sacrificial layer formed of the polyimide organic material is dissolved by use of an aprotic solvent to permit the post-formed thin films to be peeled off from the substrate along with the hydrophilic layer to obtain microbeads.

17. The method of claim 13, wherein the sacrificial layer is formed by use of a hydrophilic organic material of a type same as or different from the hydrophilic layer and the sacrificial layer formed of the hydrophilic organic material is dissolved by use of a solvent set at a temperature, at which the hydrophilic organic material is able to be re-dissolved therein, or is subjected to ultrasonic treatment in the peeling-off step to permit the post-formed thin films to be peeled off from the substrate along with the hydrophilic layer to obtain microbeads.

* * * * *

SEQUENCE LISTING

```
<160> NUMBER OF SEQ ID NOS: 5

<210> SEQ ID NO 1
<211> LENGTH: 30
<212> TYPE: DNA
<213> ORGANISM: Artificial
<220> FEATURE:
<223> OTHER INFORMATION: The nucleic acid sequence of the oligo DNA-1

<400> SEQUENCE: 1
gacaatgtgt acatcaacat cacctaccac                                          30

<210> SEQ ID NO 2
<211> LENGTH: 30
<212> TYPE: DNA
<213> ORGANISM: Artificial
<220> FEATURE:
<223> OTHER INFORMATION: The nucleic acid sequence of the oligo DNA-2
```

```
<400> SEQUENCE: 2
gacaatgtgt acatcaacat cacctaccac                                    30

<210> SEQ ID NO 3
<211> LENGTH: 30
<212> TYPE: DNA
<213> ORGANISM: Artificial
<220> FEATURE:
<223> OTHER INFORMATION: The nucleic acid sequence of the oligo DNA-3

<400> SEQUENCE: 3
gtggtaggtg atgttgatgt acacattgtc                                    30

<210> SEQ ID NO 4
<211> LENGTH: 20
<212> TYPE: DNA
<213> ORGANISM: Artificial
<220> FEATURE:
<223> OTHER INFORMATION: The nucleic acid sequence of the
      oligonucleotide for the region A

<400> SEQUENCE: 4
gagaacgatc ttcagggtgc                                               20

<210> SEQ ID NO 5
<211> LENGTH: 20
<212> TYPE: DNA
<213> ORGANISM: Artificial
<220> FEATURE:
<223> OTHER INFORMATION: The nucleic acid sequence of the
      oligonucleotide for the region B

<400> SEQUENCE: 5
cgatctaggt actgcaagta                                               20
```